(12) United States Patent
Trogler et al.

(10) Patent No.: US 7,927,881 B2
(45) Date of Patent: Apr. 19, 2011

(54) INORGANIC POLYMERS AND USE OF INORGANIC POLYMERS FOR DETECTING NITROAROMATIC COMPOUNDS

(75) Inventors: William C. Trogler, Del Mar, CA (US);
Sara A Urbas, San Diego, CA (US);
Sarah J. Toal, Rockville, MD (US);
Jason Sanchez, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 183 days.

(21) Appl. No.: 11/990,832

(22) PCT Filed: Aug. 25, 2005

(86) PCT No.: PCT/US2005/030381
§ 371 (c)(1),
(2), (4) Date: Mar. 24, 2008

(87) PCT Pub. No.: WO2007/024227
PCT Pub. Date: Mar. 1, 2007

(65) Prior Publication Data
US 2009/0137059 A1    May 28, 2009

(51) Int. Cl.
*G01N 33/44* (2006.01)
(52) U.S. Cl. .............. 436/85; 436/91; 436/92; 436/164; 436/172; 436/177; 436/178
(58) Field of Classification Search .......... None
See application file for complete search history.

(56) References Cited

U.S. PATENT DOCUMENTS

| | | | |
|---|---|---|---|
| 6,169,193 B1 | 1/2001 | West et al. | |
| 6,376,694 B1 | 4/2002 | Uchida et al. | |
| 2003/0100123 A1 | 5/2003 | Schanze et al. | |
| 2005/0101026 A1 | 5/2005 | Sailor et al. | |

FOREIGN PATENT DOCUMENTS
WO    WO 02/38653    5/2002

OTHER PUBLICATIONS

Sohn et al, Detection of TNT and picric acid on surfaces and in seawater using photoluminescent polymers containing group IV . metalloles, Abstract of Papers, 221st ACS National Meeting, San Diego, CA, United States, Apr. 1-5, 2001 INOR-589.*

(Continued)

*Primary Examiner* — Yelena G Gakh
*Assistant Examiner* — Christopher A Hixson
(74) *Attorney, Agent, or Firm* — Greer, Burns & Crain Ltd.

(57) ABSTRACT

A method for detecting an analyze that may be present in ambient air, bound to a surface or as part of complex aqueous media that includes providing a metallole-containing polymer or copolymer, exposing the polymer or copolymer to a suspected analyze or a system suspected of including the analyze, and measuring a quenching of photoluminescence of the metallole-containing polymer or copolymer exposed to the system. Also included is a solid state inorganic-organic polymer sensor for detecting nitroaromatic compounds that includes a substrate and a thin film of a metallole-containing polymer or copolymer deposited on said substrate.

12 Claims, 17 Drawing Sheets

OTHER PUBLICATIONS

Benfaremo, Nicholas et al. "Synthesis and characterization of luminescent polymers of distyrylbenzenes with oligo(ethylene glycol) spacers." Macromolecules (1998) 31 p. 3595-3599.*

Albizane, Abderrahman et al. "Organolithium route to poly(arylsilane)s." Polymer International (1991) 26 p. 93-96.*

Kim, Dong Soek et al. "Synthesis and properties of poly(silylenevinylene(bi)phenylenevinylene)s by hydrosilation polymerization." Journal of Polymer Science Part A: Polymer Chemistry (1999) 27 2933-2940.*

Honglae Sohn, Rebecca M. Calhoun, Michael J. Sailor, William C. Trogler, "Detection of TNT and Picric Acid on Surfaces and in Seawater by Using Photoluminescent Polysiloles", *Angew. Chem. Int.*, vol. 40, No. 11, 2001, pp. 2104-2105.

Honglae Sohn, Michael J. Sailor, Douglas Magde, William C. Trogler, "Detection of Nitroaromatic Explosives Based on Photoluminescent Polymers Containing Metalloles", *J. Am. Chem. Soc.*, vol. 125, 2003, pp. 3821-3830.

Jye-Shane Yang, Timothy M. Swager, "Fluorescent Porous Polymer Films as TNT Chemosensors: Electronic and Structural Effects", *J. Am. Chem. Soc.*, vol. 120, 1998, pp. 11864-11873.

Jye-Shane Yang, Timothy M. Swager, "Porous Shape Persistent Fluorescent Polymer Films: An Approach to TNT Sensory Materials", *J. Am. Chem. Soc.*, vol. 120, 1998, pp. 5321-5322.

Honglae Sohn, Michael J. Sailor, Douglas Magde, William C. Trogler, "Detection of Nitroaromatic Explosives Based on Photoluminescent Polymers Containing Metalloles", *J. American Chemical Society*, 2003, pp. 3821-3830.

* cited by examiner where R is a H or an alkyl or aryl group selected from the group consisting of Me or Ph; and where M is selected from the group consisting of Si and Ge.

| polymers | $M_w$ | $M_n$ | $\lambda_{abs}\pi-\pi^*,$ $\sigma-\sigma_2+\pi^*$ (nm) | $\lambda_{fluo}$ (nm) | $K_{SV}(M^{-1})$ PA | $K_{SV}(M^{-1})$ TNT | $K_{SV}(M^{-1})$ DNT | $K_{SV}(M^{-1})$ NB | $t(\times 10^{-9}s)$ |
|---|---|---|---|---|---|---|---|---|---|
| 1 | $6.2 \times 10^3$ | $5.4 \times 10^3$ | 368, 314 | 513 | 11 000 | 4340 | 2420 | 1200 | 0.70[c] |
| 2 | $4.6 \times 10^3$ | $4.4 \times 10^3$ | 368, 302 | 499 | 6710 | 2050 | 1010 | 320 | 0.28[d] |
| 3 | $5.5 \times 10^3$ | $5.0 \times 10^3$ | 364, 302 | 510, 385 | 8910 | 3050 | 1730 | 753 | 0.43 |
| 4 | $4.4 \times 10^3$ | $4.2 \times 10^3$ | 370, 318 | 491 | 9120 | 3520 | 2060 | 1150 | 2.33 |
| 5 | $4.5 \times 10^3$ | $4.1 \times 10^3$ | 370, 320 | 488 | 10 700 | 3940 | 2380 | 1230 | 1.34 |
| 6 | $4.8 \times 10^3$ | $4.1 \times 10^3$ | 368, 320 | 489 | 8420 | 3030 | 2010 | 735 | 2.20 |
| 7 | $5.0 \times 10^3$ | $4.8 \times 10^3$ | 364, 318 | 493 | 10 800 | 3430 | 2330 | 965 | 0.62 |
| 8 | $4.6 \times 10^3$ | $4.0 \times 10^3$ | 366, 324 | 505, 385 | 9350 | 3680 | 2340 | 864 | 2.70 |
| 9 | $4.9 \times 10^3$ | $4.4 \times 10^3$ | 364, 304 | 483, 400 | 10 300 | 3990 | 2570 | 1140 | 0.27 |
| 10 | $4.4 \times 10^3$ | $4.2 \times 10^3$ | 364, 304 | 486, 400 | 9990 | 3330 | 2000 | 965 | 0.35 |
| 11 | $4.1 \times 10^3$ | $3.9 \times 10^3$ | 364, 304 | 484, 400 | 8740 | 3430 | 2210 | 986 | 0.26 |
| 12 | $5.4 \times 10^3$ | $5.0 \times 10^3$ | 364, 306 | 480, 402 | 9840 | 3340 | 2150 | 936 | 0.22 |

FIG. 5

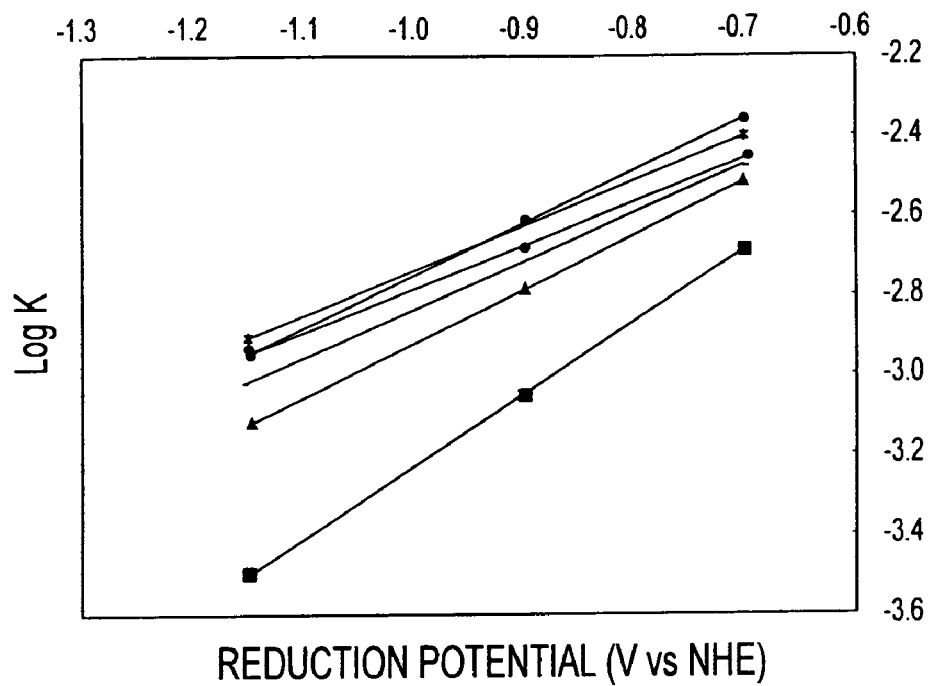
FIG. 17
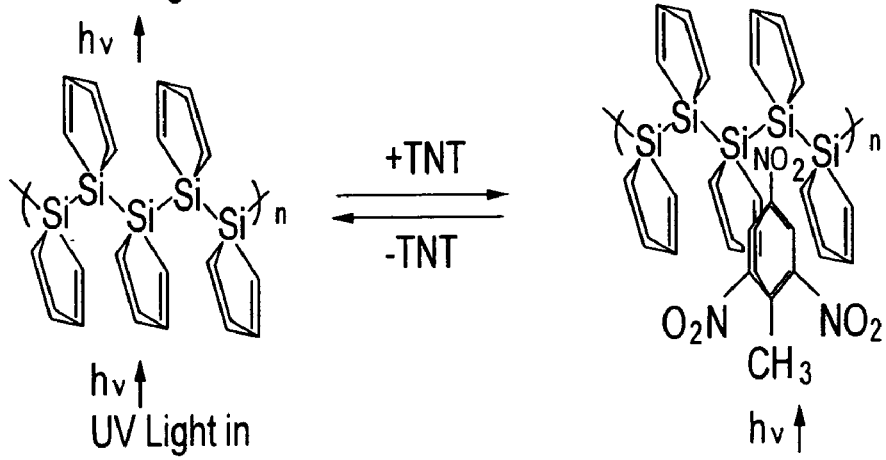
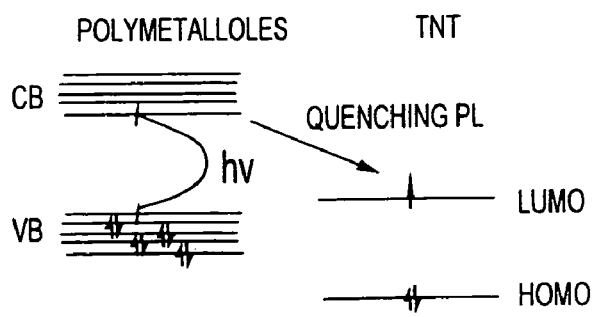
FIG. 18

|  | TNT | | DNT | | PA | |
|---|---|---|---|---|---|---|
|  | Porcelain (nm) | Paper (nm) | Porcelain (nm) | Paper (nm) | Porcelain (nm) | Paper (nm) |
| PSi | 10 | 30 | 40 | 50 | 40 | 40 |
| PDEBSi | 10 | 30 | 20 | 50 | 20 | 30 |
| PGe | 5 | 30 | 30 | 50 | 30 | 30 |
| PDEBGe | 10 | 30 | 50 | 50 | 30 | 30 |
| PSF | 5 | 30 | 20 | 40 | 5 | 5 |
| PDEBSF | 10 | 20 | 20 | 40 | 5 | 5 |

FIG. 22

INORGANIC POLYMERS AND USE OF INORGANIC POLYMERS FOR DETECTING NITROAROMATIC COMPOUNDS

STATEMENT OF GOVERNMENT INTEREST

This invention was made with Government assistance under NSF Grant No. CHE-0111376 and AFOSR MURI Grant No. F49620-02-1-0288. The Government has certain rights in this invention.

TECHNICAL FIELD

A field of the invention is analyte detection. The instant invention is directed to inorganic polymers and use of inorganic polymers, namely photoluminescent metallole-containing polymers and copolymers, for detection of nitroaromatic compounds based on photoluminescence quenching.

BACKGROUND ART

Use of chemical sensors to detect ultra-trace analytes from explosives has been the focus of investigation in recent years owing to the critical importance of detecting explosives in a wide variety of areas, such as mine fields, military bases, remediation sites, and urban transportation areas Detecting explosive analytes also has obvious applications for homeland security and forensic applications, such as the examination of post-blast residue. Typically these chemical sensors are small synthetic molecules that produce a measurable signal upon interaction with a specific analyte.

Chemical sensors are preferable to other detection devices, such as metal detectors, because metal detectors frequently fail to detect explosives, such as in the case of the plastic casing of modern land mines. Similarly, trained dogs are both expensive and difficult to maintain. Other detection methods, such as gas chromatography coupled with a mass spectrometer, surface-enhanced Raman, nuclear quadrupole resonance, energy-dispersive X-ray diffraction, neutron activation analysis and electron capture detection are highly selective, but are expensive and not easily adapted to a small, low-power package.

Conventional chemical sensors have drawbacks as well. Sensing TNT and picric acid in groundwater or seawater is important for the detection of buried, unexploded ordnance and for locating underwater mines, but most chemical sensor detection methods are only applicable to air samples because interference problems are encountered in complex aqueous media. Thus, conventional chemical sensors are inefficient in environmental applications for characterizing soil and groundwater contaminated with toxic TNT at military bases and munitions production and distribution facilities. Also, conventional chemical sensors, such as highly π-conjugated, porous organic polymers, are commonly used as chemical sensors and can be used to detect vapors of electron deficient chemicals, but require many steps to synthesize and are not selective to explosives.

Furthermore, many conventional chemical sensing methods are not amenable to manufacture as inexpensive, low-power portable devices. Additionally, these methods are limited to vapor phase detection, which is disadvantageous given the low volatility of many explosives. For example, the vapor pressure of TNT, which is approximately 5 ppb at room temperature, may be up to six times lower when enclosed in a bomb or mine casing, or when present in a mixture with other explosives.

Additionally, current routes for synthesis of polymetalloles use hazardous reagents and are of low efficiency. For example, poly(tetraphenyl)silole has been synthesized by Wurtz-type polycondensation, but the reaction yields are low.

DISCLOSURE OF INVENTION

An embodiment of the present invention is a directed device and method for detecting solid-state, vapor phase and solution phase nitroaromatic compounds using an inorganic polymer sensor, namely photoluminescent metallole-containing polymers and copolymers. The invention also includes a method for synthesizing an inorganic polymer sensor, namely photoluminescent metallole-containing copolymers.

BRIEF DESCRIPTION OF THE DRAWINGS

FIG. 5 is a table of the absorption and fluorescence spectra observed in one embodiment of the instant invention and taken at the concentrations of 2 mg/L in THF and 10 mg/L in toluene, respectively;

FIG. 17 illustrates a plot of log K vs reduction potential of analytes: ♦ (polymer 1), ■ (polymer 2), ♦ (polymer 3), ● (polymer 4), ¤ (polymer 5), and (polymer 10);

FIG. 18 illustrates a schematic diagram of electron-transfer mechanism for quenching the photoluminescence of polymetallole by analyte;

FIG. 22 is a table summarizing the detection limits of TNT, DNT, and picric acid using the five metallole-containing polymers synthesized, PSi, PDEBSi, PGe, PDEBGe, and PDEBSF;

BEST MODE FOR CARRYING OUT THE INVENTION

Figure 1:
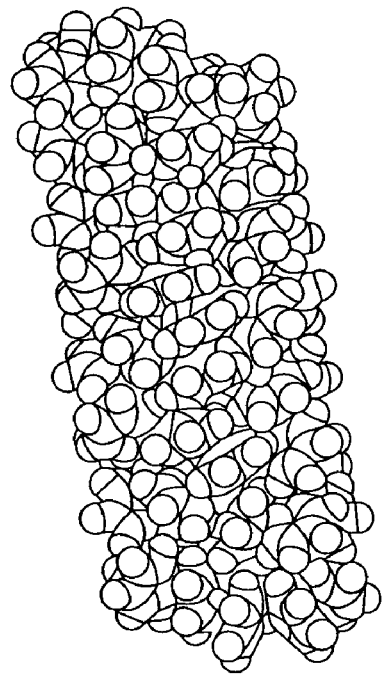
FIG. 1 is a model of a polysilole molecule.

Solid state sensing may be especially desirable for trace residue detection on surfaces believed to be contaminated, such as, for example, where filter paper is used to swab or wipe a surface of interest and the filter paper is subsequently subjected to analysis. Conventional solid state detection kits, such as that manufactured under the brand name ExPray® by Plexus Scientific Corporation of Alexandria, Va. are able to detect various explosive through a color change, with sensitivity down to the tens of nanogram level.

The vapor pressure of TNT, for example, which is approximately 5 ppb at room temperature, may be up to 6 times lower when enclosed in a bomb or mine casing or when present in mixtures with other explosives. Accordingly, embodiments of the invention include the solid-state detection of trace residue of nitroaromatics, such as picric acid (PA, 2,4,6-trinitrophenol or $C_6H_2(NO_2)_3OH$), nitrobenzene (NB or $C_6H_5NO_2$), 2,4-dinitrotoluene (DNT or $C_7H_6N_2O_4$) and 2,4,6-trinitrotoluene (TNT or $C_7H_5N_3O_6$), using thin films of luminescent metallole-containing polymers. Advantageously, detection limits as low as 5 ng are obtained. Polymetalloles and copolymers have the advantage of being inexpensive, easily prepared, and readily fielded for on-site explosives detection.

For example, one preferred embodiment includes a method for detecting an analyte that may be present in ambient air, bound to a surface or as part of complex aqueous media that includes a metallole-containing polymer or copolymer being exposed to a system suspected of containing the analyte, such as on a solid surface or in an aqueous medium. By subsequently measuring the photoluminescence of the metallole-containing polymer or copolymer, the presence, absence and approximate quantity may be determined with great sensitivity. By illuminating the polymer or copolymer with light having a wavelength of between 250 nm and 420 nm, photoluminescence quenching may be observed.

Another preferred embodiment includes a metallole-containing polymer sensor for sensing trace amounts of nitroaromatic compounds that includes a metallole-containing polymer cast, sprayed or otherwise deposited on a surface suspected of containing the nitroaromatic compounds. It is contemplated that the solid surface on which detection may occur may include a virtually boundless number of surfaces, such as glass, paper, plastic, wood, porcelain or metal, to name a few.

Additionally, embodiments of the invention include the synthesis and use of inorganic polymers, namely photoluminescent metallole-containing polymers and copolymers, in solid state or solution for detection of nitroaromatic compounds based on photoluminescence quenching. Inorganic-organic polymers may be prepared by catalytic hydrosilation or hydrogermylation with dihydrosilole or dihydrogermole compounds and organic diynes or dialkenes. The invention includes an inexpensive and highly efficient inorganic or inorganic-organic polymer sensor that can detect the existence of an analyte, namely nitroaromatic compounds such as picric acid, nitrobenzene, DNT and TNT in air, water, on surfaces, organic solution, or other complex aqueous media.

Photoluminescent metallole polymers are stable in air, water, acids, common organic solvents, and even seawater containing bioorganisms. Therefore, the inorganic polymer sensor of the instant invention includes the metallole copolymers for detection of analytes in these media. Importantly, the inorganic polymer sensors of the instant invention are insensitive to organic solvents and common environmental interferents, allowing the use of the sensor in a wide variety of environments and applications.

Metalloles are silicon (Si) or germanium (Ge)-containing metallocyclopentadienes that include one-dimensional Si—Si, Ge—Ge, or Si—Ge wires encapsulated with highly conjugated organic ring systems as side chains. Silole and germole dianions $(RC)_4Si^{2-}$ and $(RC)_4Ge^{2-}$, where R=Ph or Me, have been extensively studied by X-ray crystallography and found to be extensively delocalized. Siloles and germoles are of special interest because of their unusual electronic and optical properties, and because of their possible application as electron transporting materials in devices. Polysilanes and polygermanes containing a metal-metal backbone emit in the near UV spectral region, exhibit high hole mobility, and show high nonlinear optical susceptibility, which makes them efficient photoemission candidates for a variety of optoelectronics applications. These properties arise from a σ-σ* delocalization along the M-M backbones and confinement of the conjugated electrons along the backbone.

Polymetalloles and metallole-silane copolymers are unique in having both a M-M backbone as well as an unsaturated five-membered ring system. These polymers are highly photoluminescent, and are accordingly useful as light emitting diodes (LEDs) or as chemical sensors. Characteristic features of polymetalloles and metallole-silane copolymers include a low reduction potential and a low-lying lowest unoccupied molecular orbital (LUMO) due σ*-π* conjugation arising from the interaction between the σ* orbital of silicon or germanium and the π* orbital of the butadiene moiety of the five membered ring. In addition, the M-M backbones exhibit (σ*-σ* delocalization, which further delocalizes the conjugated metallole π electrons along the backbone. Electron delocalization in these polymers provides a means of amplification, because interaction between an analyte molecule and any position along the polymer chain is communicated throughout the delocalized chain.

Detection may be accomplished by measurement of the quenching of photoluminescence of metallole copolymers by the analyte. Sensitivity of metallole copolymers to the analytes picric acid, TNT, DNT and NB is as follows: PA>TNT>DNT>NB. A plot of log K versus the reduction potential of analytes (NB, DNT, and TNT) for each metallole copolymer yields a linear relationship, indicating that the mechanism of quenching is attributable to electron transfer from the excited metallole copolymers to the lowest unoccupied orbital of the analyte.

Excitation may be achieved with electrical or optical stimulation. If optical stimulation is used, a light source containing energy that is larger than the wavelength of luminescence emission of the polymer is preferably used. This could be achieved with, for example, a mercury lamp, a blue light emitting diode, or an ultraviolet light emitting diode.

Figure 2:
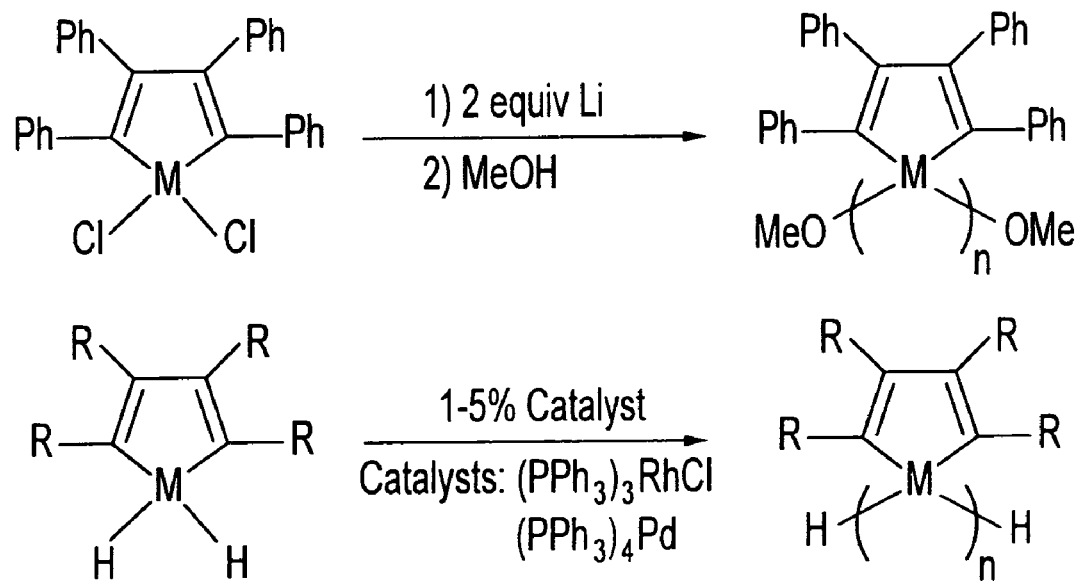
FIG. 2 illustrates a pair of equations for the synthesis of polygermole and polysilole according to an embodiment of the invention.
Figure 3:
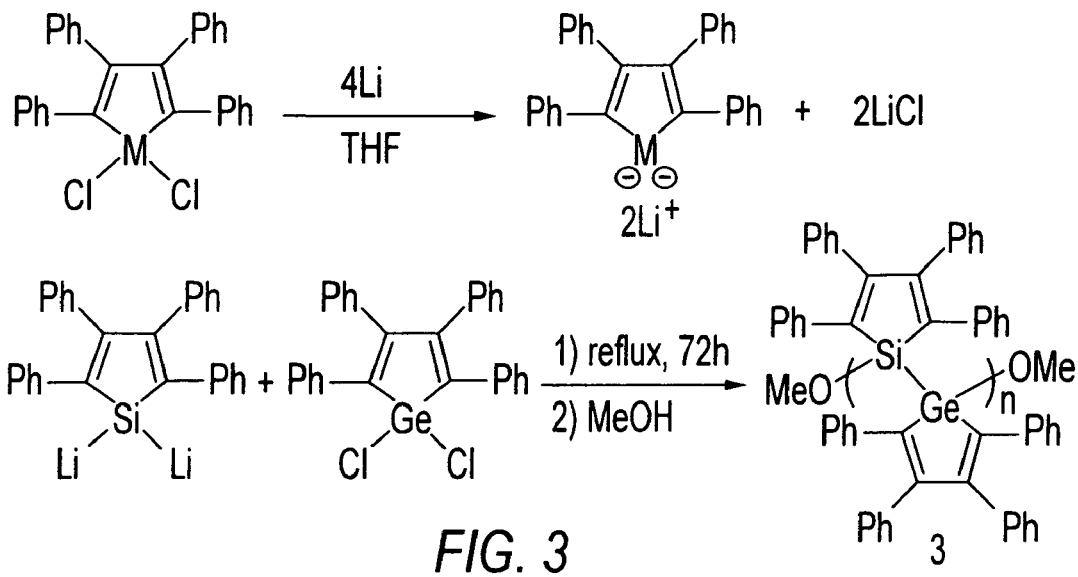
FIG. 3 illustrates a pair of equations for the synthesis of a silole-germole copolymer according to an embodiment of the invention.
Figure 4:
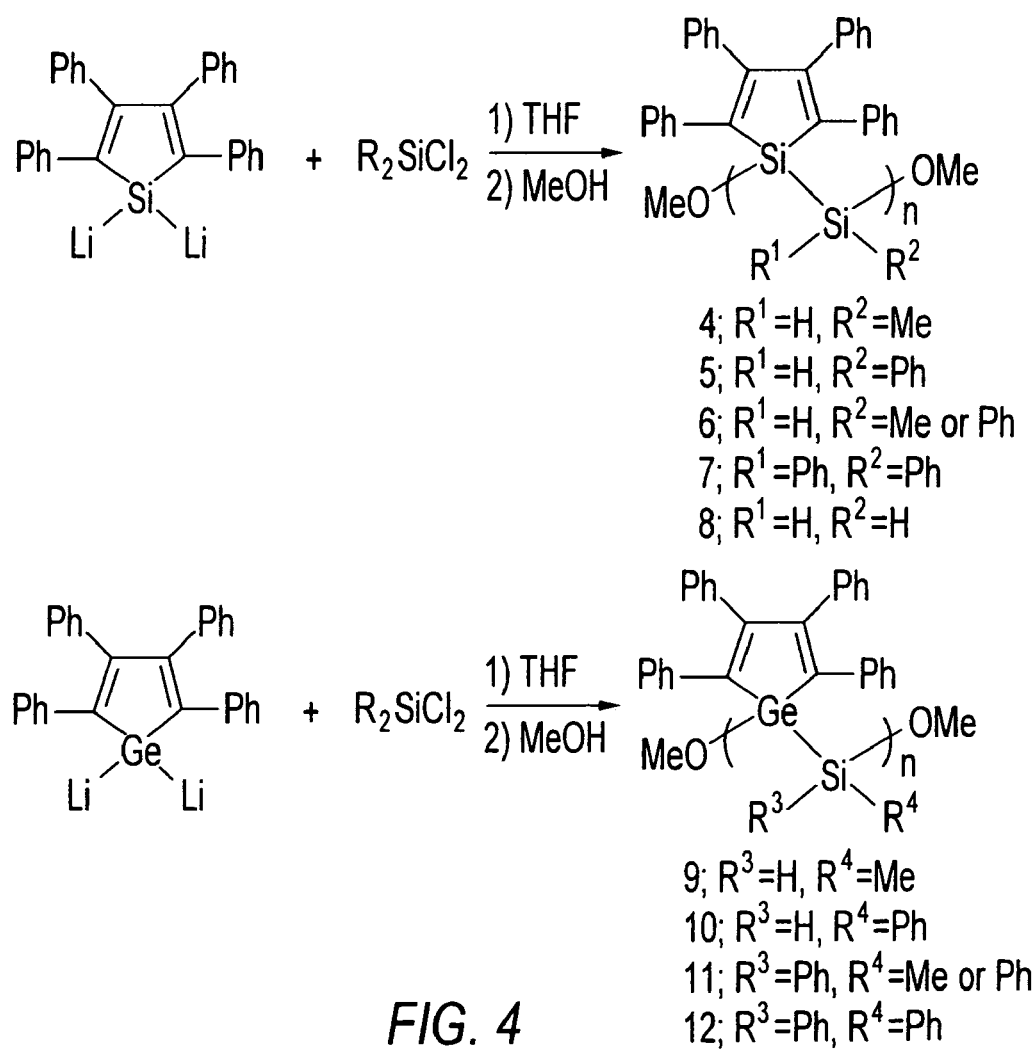
FIG. 4 illustrates a pair of equations for the synthesis of silole-silane alternating copolymers according to an embodiment of the invention.
Figure 21:
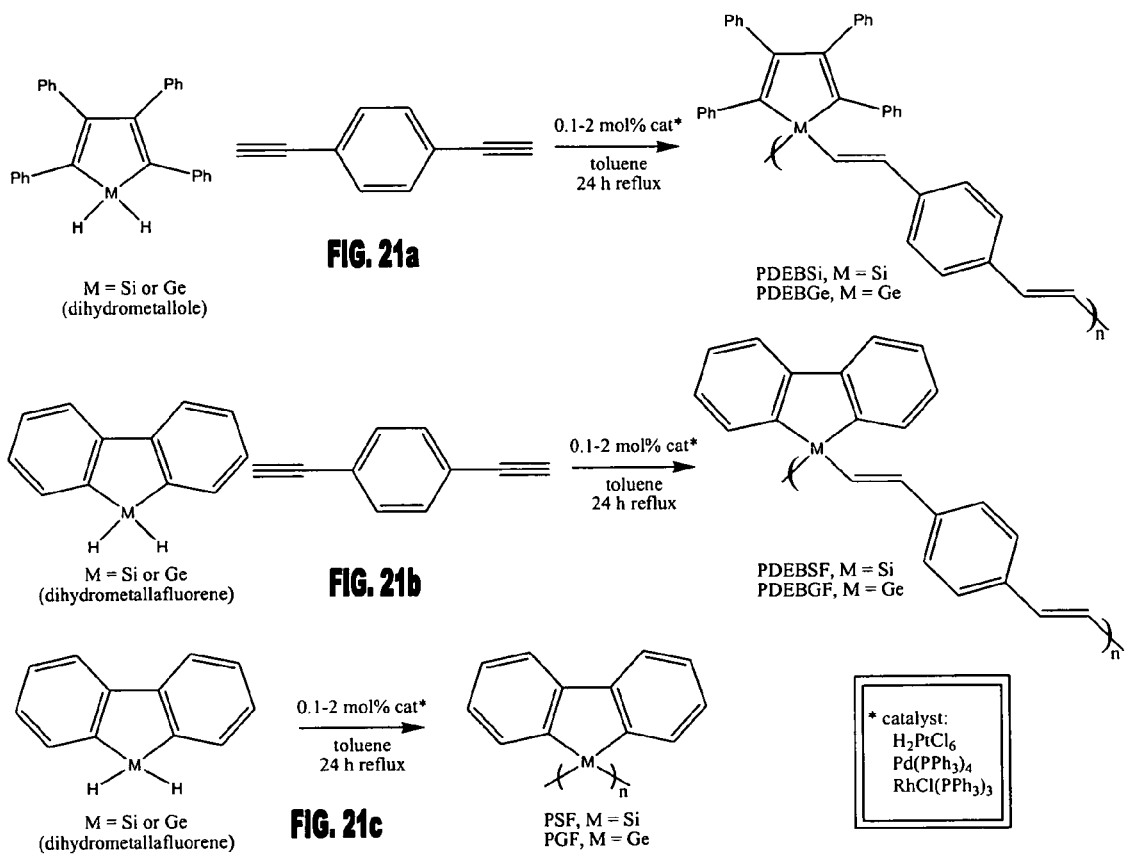
FIGS. 21a, 21b and 21c illustrate various copolymers as well as their syntheses, namely PDEBSi, PDEBGe, PDEBSF, PDEBGF, PSF and PGF.

FIG. 1 illustrates a space filling model structure of polysilole 1, which features a Si—Si backbone inside a conjugated ring system of side chains closely packed to yield a helical arrangement. FIG. 2 illustrates polymers 1 and 2, FIG. 3 illustrates polymer 3, and FIG. 4 illustrates copolymers 4-12. FIGS. 21a through 21c illustrate additional copolymers as well as their syntheses, Poly(1,4diethynylbenzene)2,3,4,5-tetraphenylsilole (PDEBsilole), Poly(1,4-diethynylbenzene)2,3,4,5-tetraphenylgermole (PDEBgermole), Poly(1,4-diethynylbenzene)silafluorene (PDEBSF), Poly(1,4-diethynylbenzene)germafluorene (PDEBGF), Polysilafluorene (PSF) and Polygermafluorene (PGF). A similar means of amplification is available to quantum-confined semiconductor nanocrystallites, via a three-dimensional crystalline network, where the electron and hole wave functions are delocalized throughout the nanocrystal.

A conventional method for preparing polymetalloles and metallole copolymers is Wurtz-type polycondensation. The syntheses of polygermole and polysiloles, and other copolymers are analogous to one another, as illustrated in equation 1 in FIG. 2, and employ the Wurtz-type polycondensation. However, yields from this method of synthesis are low (ca. ~30%). Thus, Wurtz-type polycondensation is not well-suited to large-scale production.

Embodiments of the instant invention include alternative methods for synthesizing polymetalloles that use catalytic dehydrocoupling of dihydrosiloles with a catalyst as an attractive alternative to Wurtz-type polycondensation. Bis(cyclopentadienyl) complexes of Group 4 have been extensively studied and shown to catalyze the dehydrocoupling of hydrosilanes to polysilanes for the formation of Si—Si bonds. However, only the primary organosilanes react to give polysilane. Secondary and tertiary silanes give dimers or oligomers in low yield. It has been reported that the reactivity decreases dramatically with increasing substitution at the silicon atom, since reactions catalyzed by metallocenes are typically very sensitive to steric effects. Mechanisms for dehydrogenative coupling of silanes have also been extensively investigated, which involves σ-bond metathesis.

Figure 20:
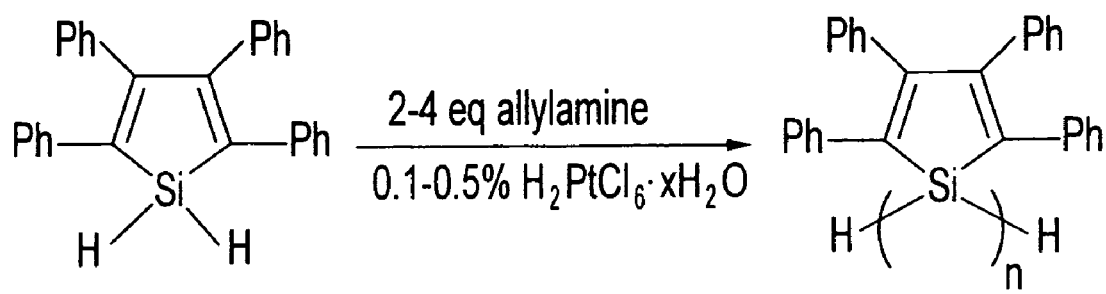
FIG. 20 illustrates an equation for a catalytic dehyrdocoupling method for synthesizing metallole polymers according to one embodiment of the invention.

Embodiments of the instant invention include catalytic dehydrocoupling of dihydrosiloles and dihydrogermoles with a catalyst. In one embodiment, the invention includes catalytic dehydrocoupling polycondensation of dihydro(tetraphenyl)silole or dihydro(tetraphenyl)germole with 1-5 mol % of Wilkinson's catalyst, $Rh(PPh_3)_3Cl$, or $Pd(PPh_3)_4$, as illustrated in FIG. 2, or 0.1-0.5 mol % of $H_2PtCl_6 \cdot xH_2O$ in conjunction with 2-5 equivalents of allylamine, or other alkene, such as cyclohexene, for example, as illustrated in FIG. 20. The latter reactions produce the respective polysilole or polygermole in high yield (ca. 80-90%). By $^1H$ NMR spectroscopy, the monomer, dihydrometallole, was completely consumed in the reaction. Molecular weights ($M_w$) of 4000-6000 are obtained, similar to those obtained by the Wurtz-type polycondensation (ca. ~30%).

Turning now to FIG. 3, silole-germole alternating copolymer 3, in which every other silicon or germanium atom in the polymer chain is also part of a silole or germole ring, was synthesized from the coupling of dichloro(tetraphenyl)germole and dilithio(tetraphenyl)silole. The latter is obtained in 39% yield from dichlorotetraphenylsilole by reduction with lithium, as illustrated in the equation of FIG. 3. The molecular weight of the silole-germole copolymer, $M_w=5.5\times10^3$, $M_n=5.0\times10^3$ determined by SEC (size exclusion chromatography) with polystyrene standards, is similar to that of polysiloles or polygermoles. All of the polymetalloles are extended oligomers with a degree of polymerization of about 10 to 16, rather than a true high $M_w$ polymer; however, they can be cast into a thin film from solution and show polymer-like properties.

Also illustrated in FIG. 4 are silole-silane alternating copolymers 4, 5, 6, 7, 8, which were also prepared from coupling of the silole dianion $(Ph_4C_4Si)Li_2$ with the corresponding silanes. Germole-silane alternation copolymers 9, 10, 11, 12 were also synthesized from the coupling of the germole dianion $(Ph_4C_4Ge)Li_2$ with the corresponding silanes, as illustrated in FIG. 4. These reactions generally employ reflux conditions in tetrahydrofuran under an argon atmosphere for about 72 hours. Some silole-silane copolymers have been synthesized previously and shown to be electroluminescent. Metallole-silane copolymers were developed so that they could be easily functionalized along the backbone by hydrosilation. The molecular weight of metallole-silane copolymers, $M_w=4.1\times10^3\sim6.2\times10^3$, $M_n=4.1\times10^3\sim5.4\times10^3$ determined by SEC, is similar to that of the polymetalloles.

The molecular weights and polydisperity indices (PDI) of polymers 1-12 (FIG. 4) determined by gel permeation chromatography (GPC) are illustrated in Table 1 of FIG. 5.

Inorganic-organic poly(1,4-diethynylbenzene)metallole (DEB) type polymers may be obtained by hydrosilation of an dialkyne, specifically DEB, with a dihydrometallole using a catalyst such as chloroplatinic acid. FIGS. 21a-21c illustrate the reaction whereby the DEB type polymers are obtained according to embodiments of the invention. A reasonable extension of this principle includes hydrosilation and hydrogermylation of any organic diyne. A reasonable interpolation of this principle includes hydrosilation and hydrogermylation of organic dialkenes to obtain less conjugated polymers.

Absorption And Fluorescence

Figure 6:
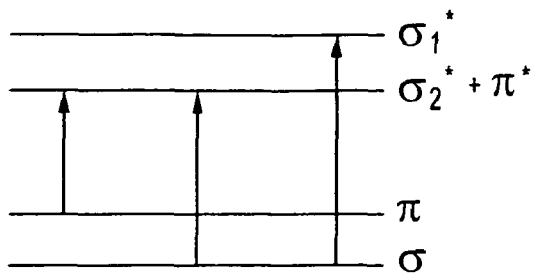
FIG. 6 is a schematic energy level diagram illustrating energy-levels for polymetalloles and metallole-silane copolymers.

The UV-vis absorption and fluorescence spectral data for polymers 1-12 are also illustrated in Table 1 of FIG. 5. The poly(tetraphenyl)metalloles 1-3 and tetraphenylmetallole-silane copolymers 4-12 exhibit three absorption bands, which are ascribed to the $\pi$-$\pi^*$ transition in the metallole ring and the $\sigma$-$(\sigma^*+\pi^*)$ and $\sigma$-$\sigma^*$ transitions in the M-M backbone. FIG. 6 illustrates a schematic energy-level diagram for polymetalloles and metallole-silane copolymers.

Figure 7:
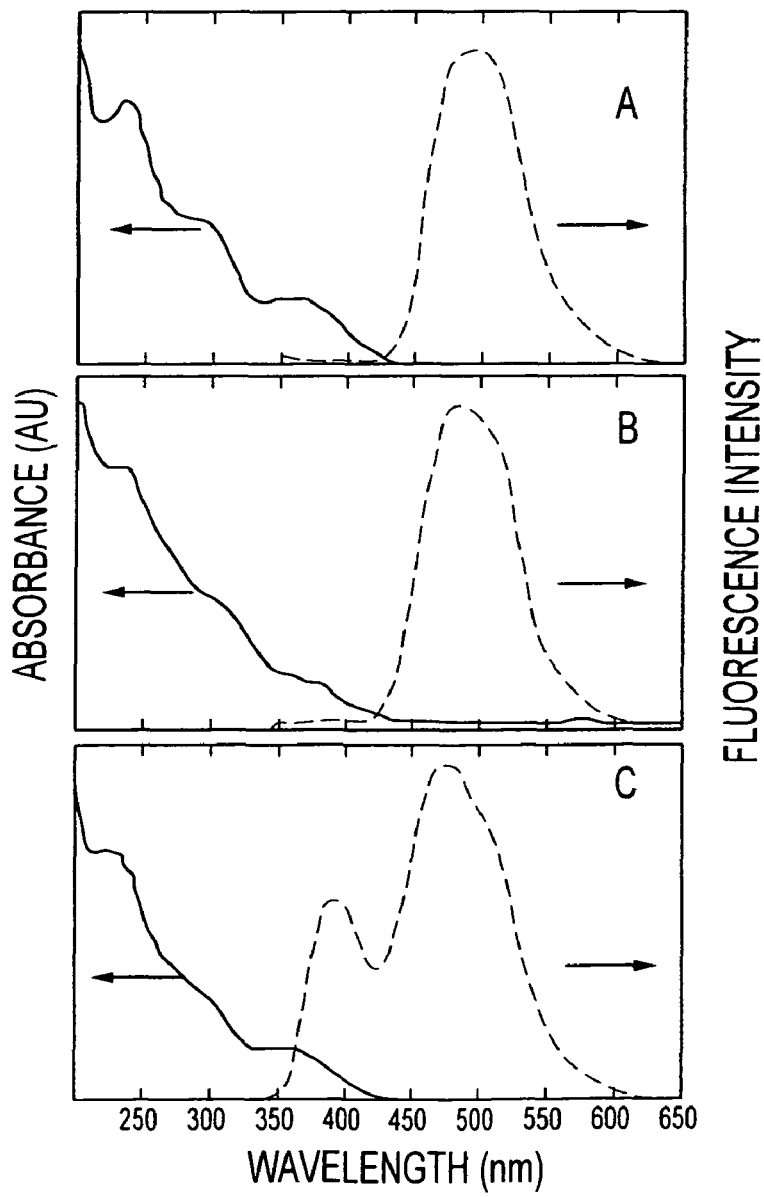
FIG. 7 is a graphical representation of UV-vis absorption spectra in THF (solid line) and fluorescence spectra in toluene (dotted line) for (A) poly(tetraphenyl) germole 2. (B) silole-silane copolymer 4, and (C) germole-silane copolymer 9.

UV-vis absorption in THF (solid line) and fluorescence spectra in toluene (dotted line) for poly(tetraphenygermole) 2, silole-silane copolymer 4 and germole-silane copolymer 9 are shown in FIG. 7. Absorptions at a wavelength of about 370 nm for the poly(tetraphenylmetallole)s 1-3 and tetraphenylmetallole-silane copolymers 4-12 are ascribed to the metallole π-π* transition of the metallole moiety, which are about 89 to 95 nm red-shifted relative to that of oligo[1,1-(2,3,4,5-tetramethylsilole)] ($\lambda_{max}$=275 nm) and are about 75 to 81 nm red-shifted relative to that of oligo[1,1-(2,5-dimethyl-3,4-diphenylsilole)] ($\lambda_{max}$=289 nm). These red shifts are attributed to an increasing main chain length and partial conjugation of the phenyl groups to the silole ring.

Figure 8A:
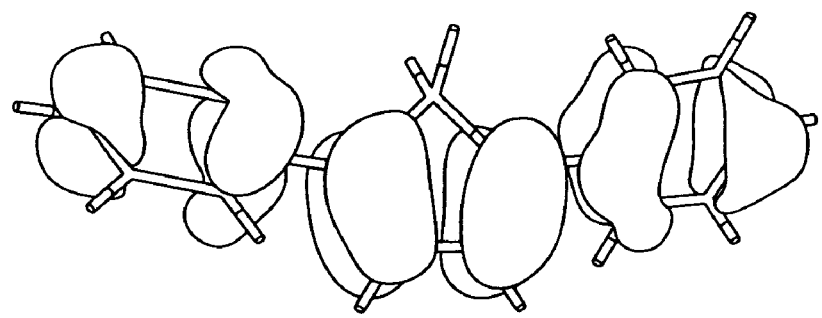
FIGS. 8A and 8B illustrate a HOMO (A) and LUMO (B) of 2,5-diphenylsilole, $Ph_2C_4SiH_2$ from the ab initio calculations at the HF/6-31G* level.
Figure 8B:
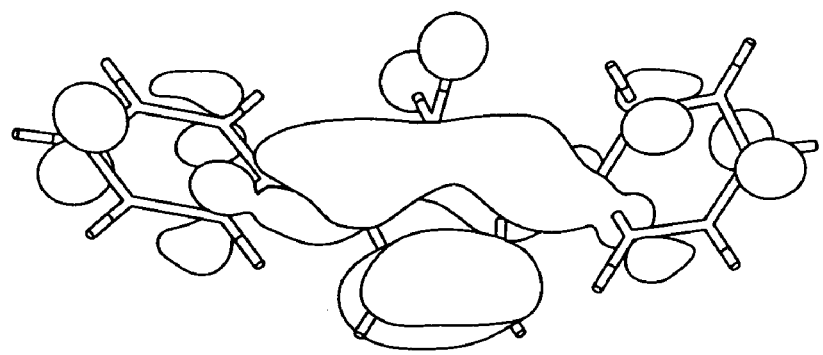

FIG. 8 shows the HOMO (A) and LUMO (B) of 2,5-diphenylsilole, Ph2C4SiH2, from the ab initio calculations at the HF/6-31G* level. Phenyl substituents at the 2,5 metallole ring positions may π-conjugate with the metallole ring LUMO. Second absorptions at wavelengths of 304 to 320 nm for the poly(tetraphenylmetallole)s 2-3 and tetraphenylmetallole-silane copolymers 4-12 are assigned to the σ–(σ2*+π*) transition, which parallels that of the poly(tetraphenyl) silole 1.

Figure 9:
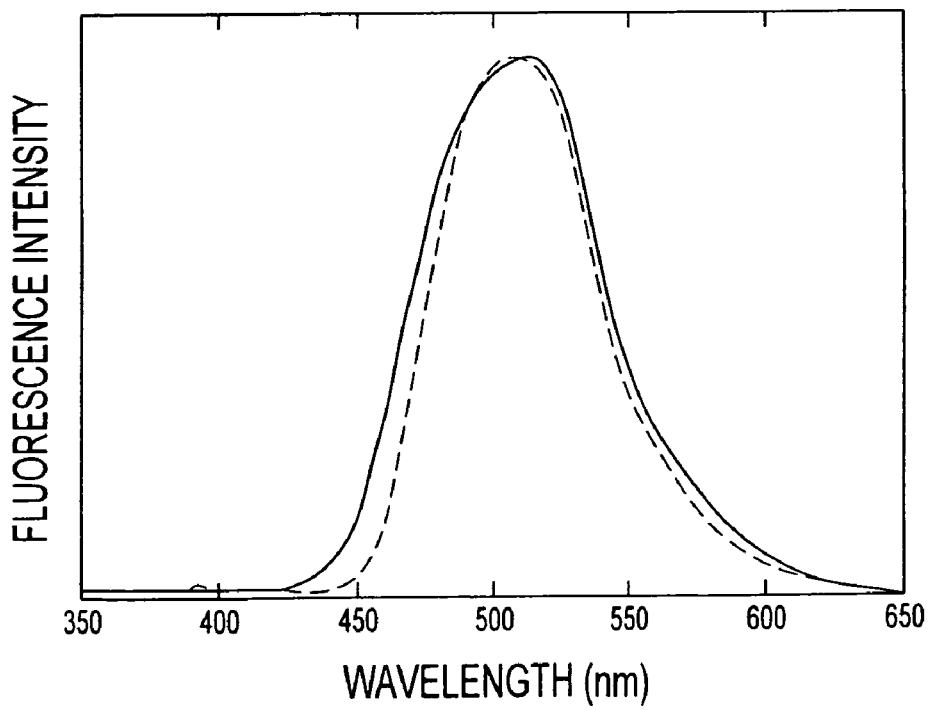
FIG. 9 is a graphical representation of the fluorescence spectra of polysilole 1 in toluene solution (solid line) and in thin solid film (dotted line)

Polymetallole 1-2 and silole-silane copolymers 4-7 exhibit one emission band ($\lambda_{max}$, 486 to 513 nm) when excited at 340 nm, whereas the others exhibit two emission bands with $\lambda_{max}$ of 480-510 nm and 385-402 nm. The ratios of the two emission intensities are not concentration dependent, which indicates that the transition does not derive from an excimer. Emission peaks for germole-silane copolymers 9-12 are only 2 to 33 nm blue-shifted compared to the other polymers. FIG. 9 shows fluorescence spectra of the poly(tetraphenyl)silole in toluene solution (solid line) and in the solid state (dotted line). The bandwidth of the emission spectrum in solution is slightly larger than in the solid state. There is no shift in the maximum of the emission wavelength. This suggests that the polysilole exhibits neither π-stacking of polymer chains nor excimer formation.

The angles of C-M-C of dihydro(tetraphenyl)silole and dihydro(tetraphenyl)germole are 93.11° on C—Si—C and 89.760 on C—Ge—C, respectively. Polymerization might take place, since the tetraphenylmetalloles have small angles at C-M-C in the metallocyclopentadiene ring, which results in less steric hindrance at the metal center. In addition, the bulky phenyl groups of silole might prevent the formation of cyclic hexamer, which is often problematic in polysilane syntheses. Cyclic polymetallole product formation was not observed.

Fluorescence Quenching With Nitroaromatic Analytes

The method of detection of the instant invention includes using a chemical sensor, namely a variety of photoluminscent copolymers having a metalloid-metalloid backbone such as Si—Si, Si—Ge, or Ge—Ge, or alternatively an inorganic-organic metallole-containing copolymer. While polymetalloles in various forms may be used to detect analytes, one embodiment includes casting a thin film of the copolymers is employed in detecting the analyte, e.g., picric acid, DNT, TNT and nitrobenzene. Detection is achieved by measuring the quenching of the photoluminescence of the copolymer by the analyte. Accordingly, the instant invention contemplates use of the polymetallole polymers and copolymers in any form susceptible to measurement of photoluminescence quenching. For example, since it is possible to measure fluorescence of solutions, other embodiments of the instant method of detection may optionally include a polymetallole in solution phase, where powdered bulk polymer is dissolved in solution. Yet another embodiment includes producing a colloid of the polymer, which is a liquid solution with the polymer precipitated and suspended as nanoparticles.

Figure 10:
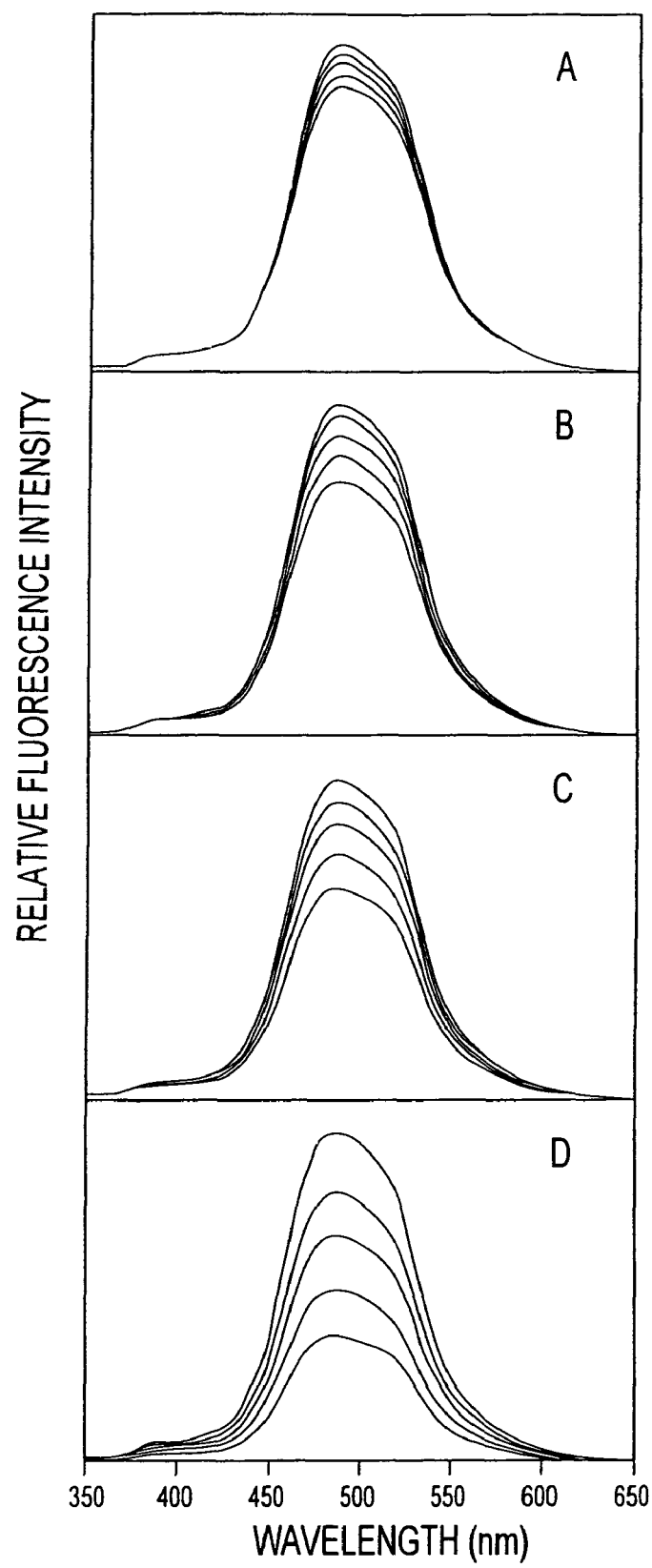
FIG. 10 is a graphical representation of the quenching of photoluminescence spectra of silole-silane copolymer 5 with (A) nitrobenzene, from top $2.0 \times 10^{-5}$ M, $3.9 \times 10^{-5}$ M, $7.8 \times 10^{-5}$ M, and $11.5 \times 10^{-5}$ M, (B) DNT, from top $1.4 \times 10^{-5}$ M, $3.9 \times 10^{-5}$ M, $7.8 \times 10^{-5}$ M, and $12.4 \times 10^{-5}$ M, (C) TNT, from top $2.1 \times 10^{-5}$ M, $4.2 \times 10^{-5}$ M, $8.1 \times 10^{-5}$ M, and $12.6 \times 10^{-5}$ M, (D) picric acid, from top $2.1 \times 10^{-5}$ M, $4.2 \times 10^{-5}$ M, $8.0 \times 10^{-5}$ M, and $12.6 \times 10^{-5}$ M.

The detection method involves measurement of the quenching of photoluminescence of the polymetalloles 1-3 and metallole-silane copolymers 4-12 by the analyte, such as a toluene solution (using a Perkin-Elmer LS 50B fluorescence spectrometer, 340 nm excitation wavelength). For example, turning now to FIG. 10, when used to detect TNT, fluorescence spectra of a toluene solution of the metallole copolymers were obtained upon successive addition of aliquots of TNT. Photoluminescence quenching of the polymers 1-12 in toluene solutions were also measured with nitrobenzene, DNT, TNT and nitrobenzene. The relative efficiency of photoluminescence quenching of metallole copolymers is unique for TNT, DNT, and nitrobenzene, respectively, as indicated in FIG. 10 by the values of K determined from the slopes of the steady-state Stern-Volmer plots. FIG. 10 demonstrates that each copolymer has a unique ratio of quenching efficiency to the corresponding analyte.

The purity of the TNT sample was found to be important to obtain reproducible results. It was synthesized by nitration of dinitrotoluene and recrystallized twice from methanol. A third recrystallization produces the same results as the twice-recrystallized material. When the quenching experiment was undertaken without recrystallization of TNT, higher (ca. 10x) quenching percentages are obtained. Presumably, impurities with higher quenching efficiencies are present in crude TNT.

The Stern-Volmer equation, which is $(I_O/I)-1=K_{SV}[A]$, is used to quantify the differences in quenching efficiency for various analytes. In this equation, $I_O$ is the initial fluorescence intensity without analyte, and I is the fluorescence intensity with added analyte of concentration [A], and $K_{SV}$ is the Stern-Volmer constant.

Figure 11A:
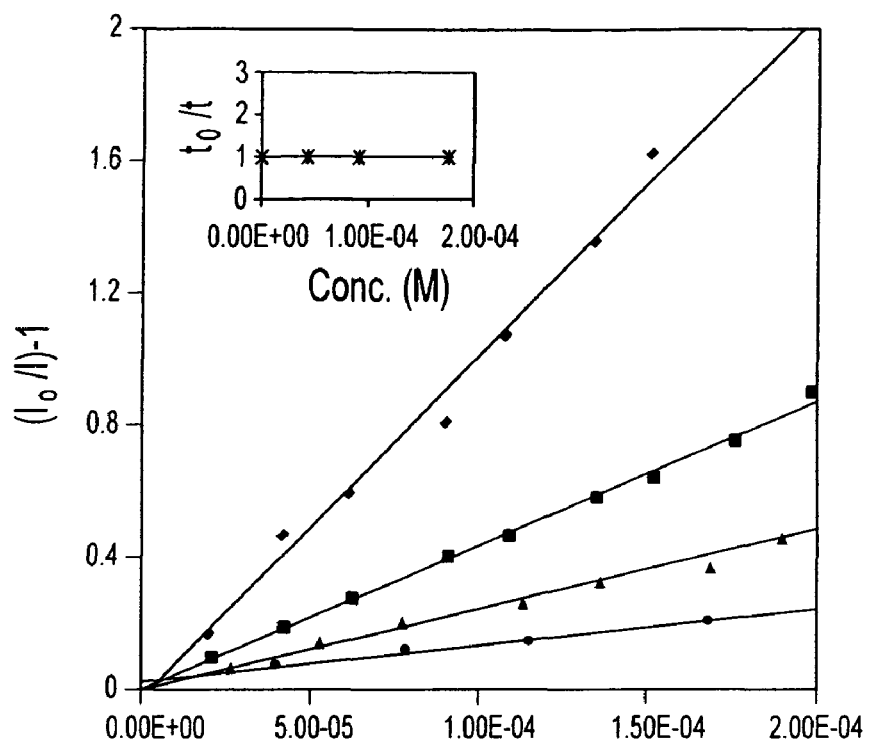
FIGS. 11A, 11B and 11C are Stern-Volmer plots; from top polysilole 1, polygermole 2, and silole-silane copolymer 8; ♦ (picric acid), ■ (TNT), ♦ (DNT), ● (nitrobenzene); the plots of fluorescence lifetime ($\tau_o/\tau$), shown as inset, are independent of added TNT.
Figure 11B:
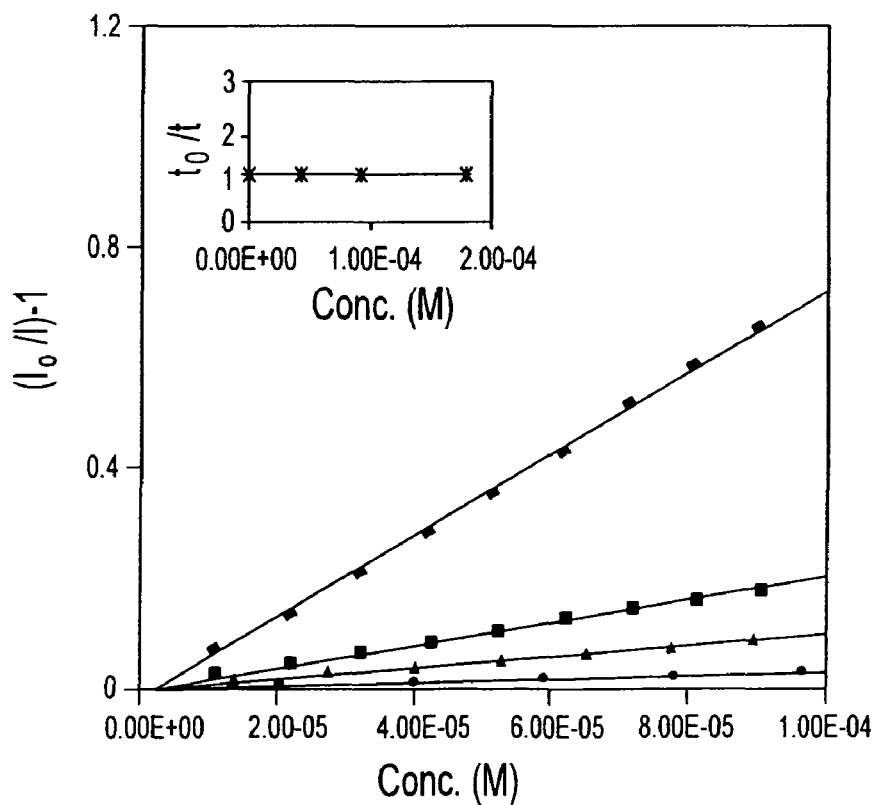
Figure 11C:
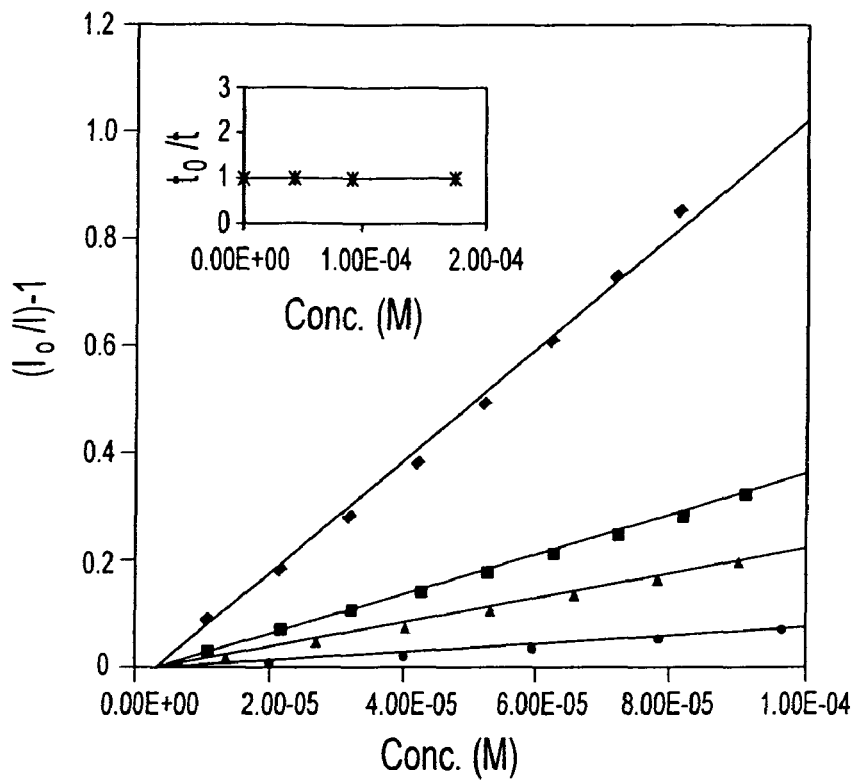

FIG. 11 shows the Stern-Volmer plots of polysilole 1, polygermole 2, and silole-silane copolymer 8 for each analyte. A linear Stern-Volmer relationship was observed in all cases, but the Stern-Volmer plot for picric acid exhibits an exponential dependence when its concentration is higher than $1.0 \times 10^{-4}$ M. A linear Stern-Volmer relationship may be observed if either static or dynamic quenching process is dominant. Thus, in the case of higher concentrations of picric acid, the two processes may be competitive, which results in a nonlinear Stern-Volmer relationship. This could also arise from aggregation of analyte with chromophore.

Photoluminescence may arise from either a static process, by the quenching of a bound complex, or a dynamic process, by collisionally quenching the excited state. For the former case, $K_{SV}$ is an association constant due to the analyte-preassociated receptor sites. Thus, the collision rate of the analyte is not involved in static quenching and the fluorescence lifetime is invariant with the concentration of analyte. With dynamic quenching, the fluorescence lifetime should diminish as quencher is added.

A single "mean" characteristic lifetime (τ) for polymetalloles and metallole-silane copolymers 1-12 has been measured and summarized in Table 1 of FIG. 5. Luminescence decays were not single-exponential in all cases. Three lifetimes were needed to provide an acceptable fit over the first few nanoseconds. The amplitudes of the three components were of comparable importance (the solvent blank made no contribution). These features suggest that the complete description of the fluorescence is actually a continuous distribution of decay rates from a heterogeneous collection of chromophore sites. Because the oligomers span a size distribution, this behavior is not surprising. The mean lifetime parameter reported is an average of the three lifetimes determined by the fitting procedure, weighted by their relative amplitudes. This is the appropriate average for comparison with the "amount" of light emitted by different samples under different quenching conditions, as has been treated in the literature. Given this heterogeneity, possible long-lived luminescence that might be particularly vulnerable to quenching has been a concern. However, measurements with a separate nanosecond laser system confirmed that there were no longer-lived processes other than those captured by the time-correlated photon counting measurement and incorporated into Table 1 of FIG. 5.

Figure 12:
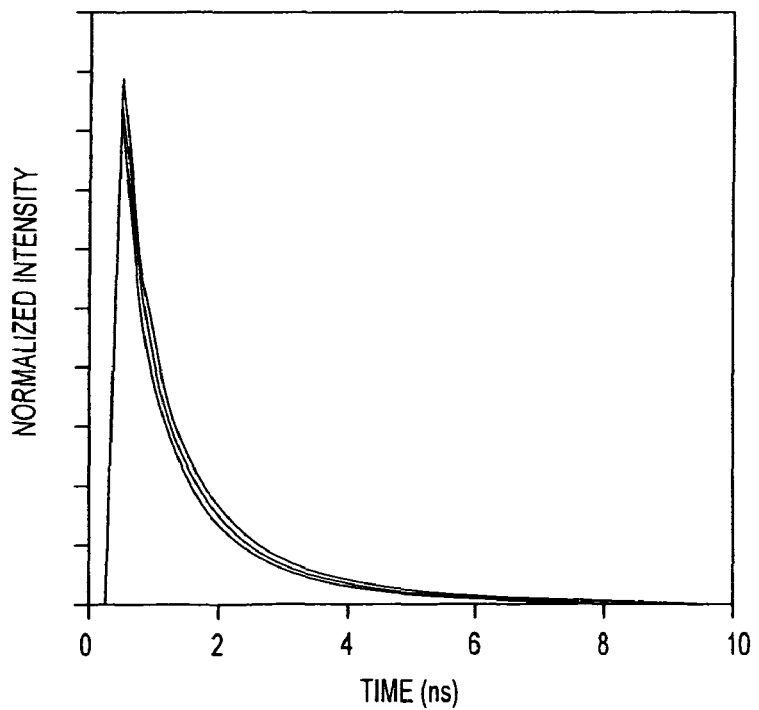
FIG. 12 illustrates fluorescence decays of polysilole 1 for different concentrations of TNT: 0 M, $4.24 \times 10^{-5}$ M, $9.09 \times 10^{-5}$ M, $1.82 \times 10^{-4}$ M.

It is notable that polysilole 1 and silole-silane copolymers 4-8 have about 3 to 11 times longer fluorescence lifetimes than polygermole 2 and germole-silane copolymers 9-12. Fluorescence lifetimes in the thin films (solid state) for polysilole 1 and polygermole 2 are 2.5 and 4.2 times longer than in toluene solution, respectively. The fluorescence lifetimes as a function of TNT concentration were also measured and are shown in the inset of FIG. 11 for polymers 1, 2, and 8. No change of mean lifetime was observed by adding TNT, indicating that the static quenching process is dominant for polymetalloles and metallole-silane copolymers 1-12 (FIG. 12). Some issues with such analyses have been discussed in the literature. This result suggests that the polymetallole might act as a receptor and a TNT molecule would intercalate between phenyl substituents of the metallole moieties (FIG. 1).

Figure 13:
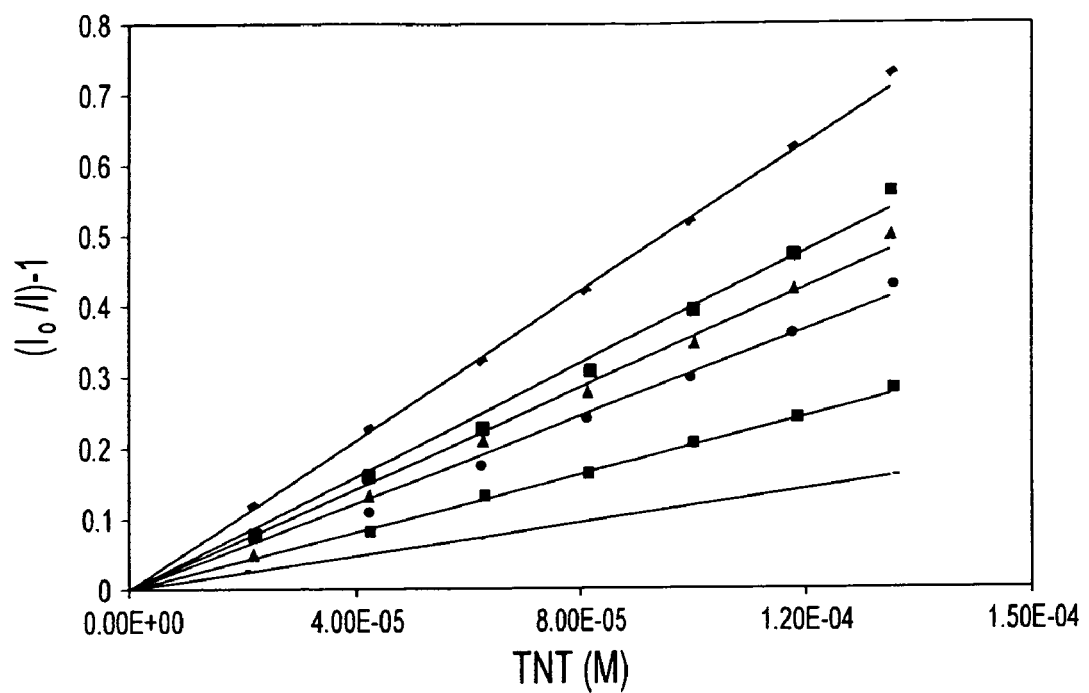
FIG. 13 illustrates Stern-Volmer plots of polymers ♦ (polymer 1), ■ (polymer 5), ♦ (polymer 4), ● (polymer 6), ⌑ (polymer 2), and — (organic pentiptycene-derived polymer 13), for TNT.
Figure 14:
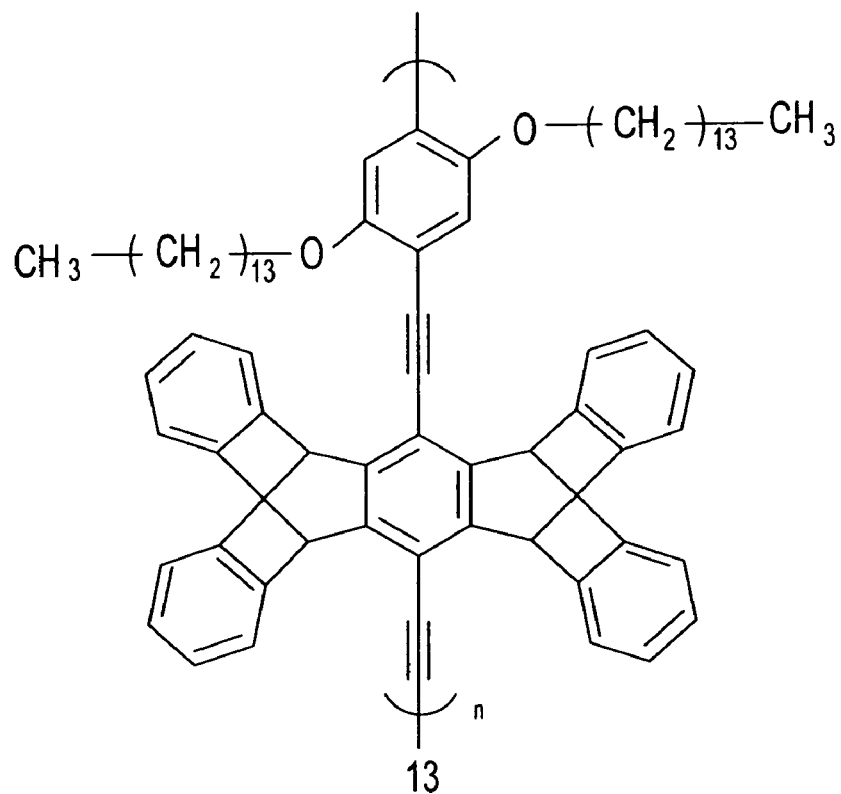
FIG. 14 illustrates a structure of the pentiptycene-derived polymer.

For chemosensor applications, it is useful to have sensors with varied responses. Each of the 12 polymers exhibits a different ratio of the photoluminescence quenching for picric acid, TNT, DNT, and nitrobenzene and a different response with the same analyte. The use of sensor arrays is inspired by the performance of the olfactory system to specify an analyte. FIG. 13 displays the Stern-Volmer plots of polymers 1, 2, 4, 5, and 6 for TNT, indicating that the range of photoluminescence quenching efficiency for TNT is between $2.05 \times 10^3$ and $4.34 \times 10^3$ $M^{-1}$. The relative efficiencies of photoluminescence quenching of poly(tetraphenylmetallole)s 1-3 and tetraphenyl-metallole-silane copolymers 4-12 were obtained for picric acid, TNT, DNT, and nitrobenzene, as indicated by the values of Ksv determined from the slopes of the steady-state Stern-Volmer plots and summarized in Table 1 of FIG. 5. Polymer 13, which is illustrated in FIG. 14, is an organic pentiptycene-derived polymer for comparison. The metallole copolymers are more sensitive to TNT than the organic pentiptycene-derived polymers in toluene solution. For example, polysilole 1 ($4.34 \times 10^3$ $M^{-1}$) has about a 370% better quenching efficiency with TNT than organic pentiptycene-derived polymer ($1.17 \times 10^3$ $M^{-1}$).

Figure 15:
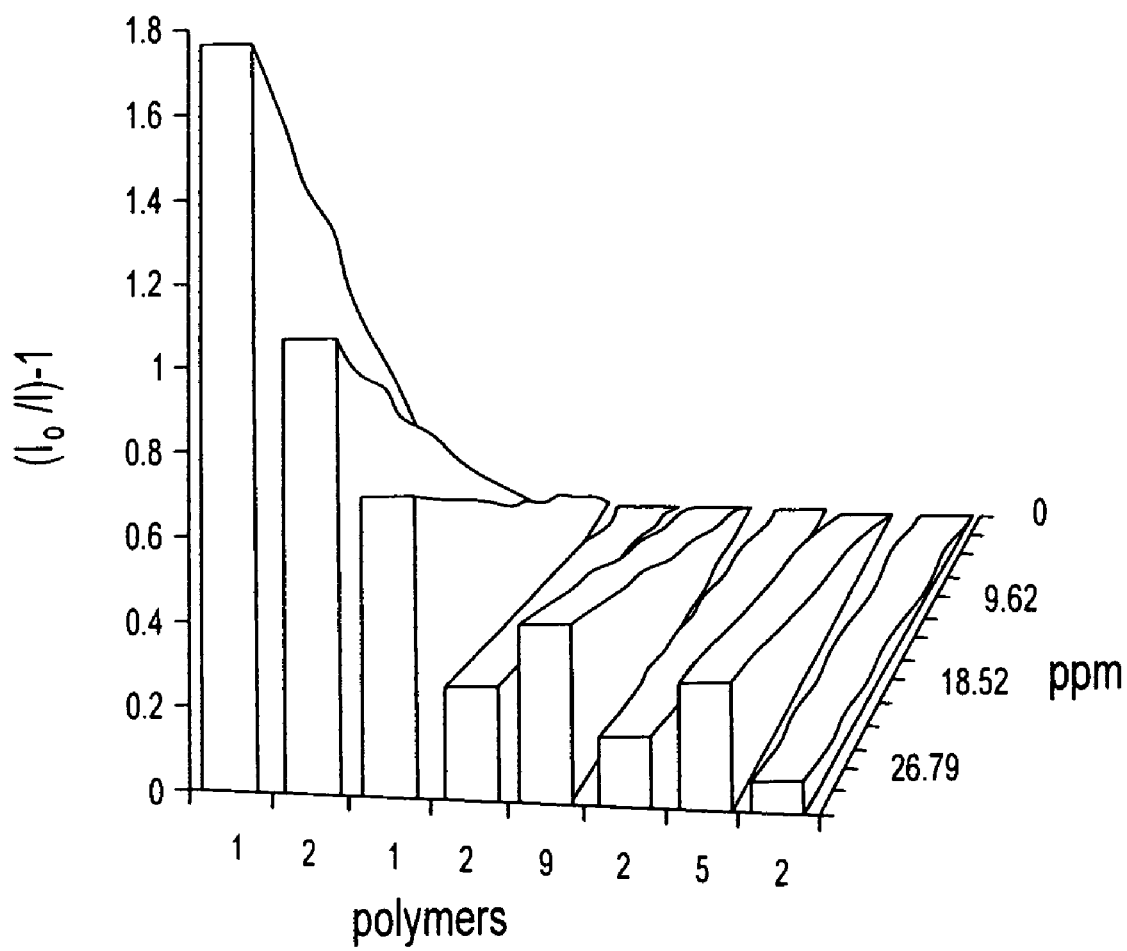
FIG. 15 illustrates, from left to right, highest and lowest photoluminescence quenching efficiency for picric acid (leftmost two lines), TNT (two lines immediately to the right of picric acid), DNT (two lines immediately to the right of TNT), and nitrobenzene (right-most two lines) showing how the varying polymer response to analyte could be used to distinguish analytes from each other.
Figure 16:
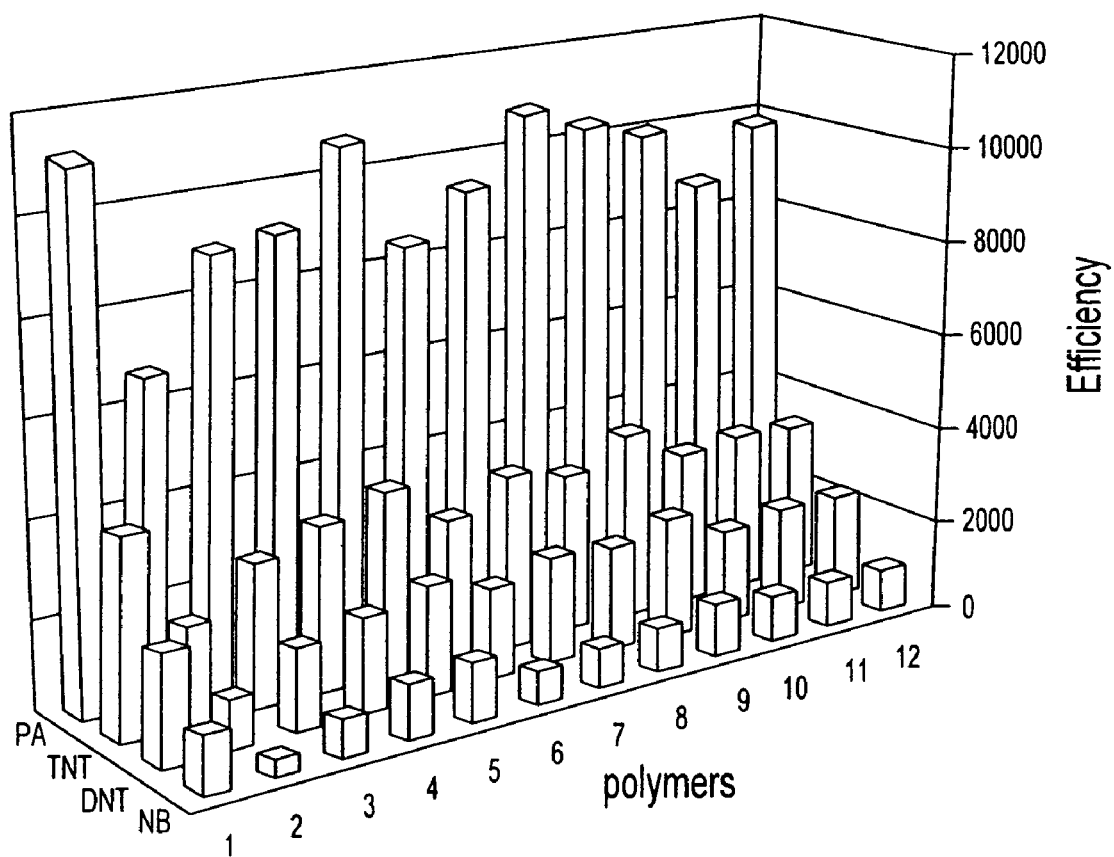
FIG. 16 illustrates a comparison of the photoluminescence quenching constants (from Stern-Volmer plots) of polymers 1-12 with different nitroaromatic analytes.

The trend in Stern-Volmer constants usually reflects an enhanced charge-transfer interaction from metallole polymer to analyte. For example, the relative efficiency of photoluminescence quenching of polysilole 1 is about 9.2:3.6:2.0:1.0 for picric acid, TNT, DNT, and nitrobenzene, respectively. Although polysilole 1 shows best photoluminescence quenching efficiency for picric acid and TNT, polymer 9 and 5 exhibit best quenching efficiency for DNT and nitrobenzene, respectively. (FIG. 15) Polygermole 2 has the lowest quenching efficiency for all analytes. Since the polymers 1-12 have similar molecular weights, the range of quenching efficiencies with the same analyte would be expected to be small. Polysilole 1 ($11.0 \times 10^3$ $M^{-1}$ and $4.34 \times 10^3$ $Me^{-1}$) exhibits 164% and 212% better quenching efficiency than polygermole 2 ($6.71 \times 10^3$ $M^{-1}$ and $2.05 \times 10^3$ $M^{-1}$) with picric acid and TNT, respectively. Polymer 9 ($2.57 \times 10^3$ $M^{-1}$) has 253% better quenching efficiency than polymer 2 ($1.01 \times 10^3$ $M^{-1}$) with DNT. Polymer 5 ($1.23 \times 10^3$ $M^{-1}$) has 385% better quenching efficiency than metallole polymer 2 ($0.32 \times 10^3$ $M^{-1}$) with nitrobenzene. FIG. 16 illustrates how an analyte might be specified using an array of multi-sensors.

FIG. 17 shows a plot of log Ksv vs. reduction potential of analytes. All metallole polymers exhibit a linear relationship, even though they have different ratios of photoluminescence quenching efficiency to analytes. This result indicates that the mechanism of photoluminescence quenching is primarily attributable to electron transfer from the excited metallole polymers to the LUMO of the analyte. Because the reduction potential of TNT (–0.7 V vs NHE) is less negative than that of either DNT (–0.9 V vs NHE) or nitrobenzene (–1.15 V vs NHE), it is detected with highest sensitivity. A schematic diagram of the electron-transfer mechanism for the quenching of photoluminescence of the metallole polymers with analyte is shown in FIG. 18. Optical excitation produces an electron-hole pair, which is delocalized through the metallole copolymers. When an electron deficient molecule, such as TNT is present, electron-transfer quenching occurs from the excited metallole copolymer to the LUMO of the analyte. The observed dependence of Ksv on analyte reduction potential suggests that for the static quenching mechanism, the polymer-quencher complex luminescence intensity depends on the electron acceptor ability of the quencher. An alternative explanation would be that the formation constant (Ksv) of the polymer-quencher complex is dominated by a charge-transfer interaction between polymer and quencher and that the formation constant increases with quencher electron acceptor ability.

Figure 19:
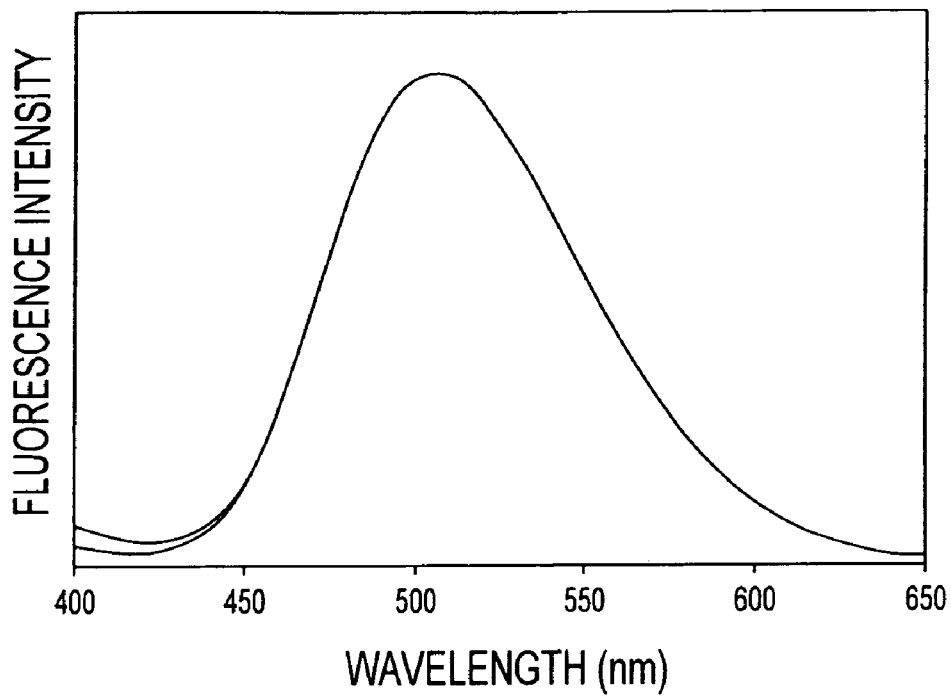
FIG. 19 illustrates an absence of quenching of photoluminescence by polysilole 1 with 4 parts per hundred of THF.

An important aspect of the metallole copolymers is their relative insensitivity to common interferents. Control experiments using both solutions and thin films of metallole copolymers (deposited on glass substrates) with air displayed no change in the photoluminescence spectrum. Similarly, exposure of metallole copolymers both as solutions and thin films to organic solvents such as toluene, THF, and methanol or the aqueous inorganic acids $H_2SO_4$ and HF produced no significant decrease in photoluminescence intensity. FIG. 19 shows that the photoluminescence spectra of polysilole 1 in toluene solution display no quenching of fluorescence with 4 parts per hundred of THF. The ratio of quenching efficiency of polysilole 1 with TNT vs benzoquinone is much greater than that of polymer 13. The Ksv value of $4.34 \times 10^3$ $M^{-1}$ of polysilole 1 for TNT is 640% greater than that for benzoquinone (Ksv=674 $M^{-1}$)$^{-1}$ The organic polymer 13, however, only exhibits a slightly better quenching efficiency for TNT (Ksv=$1.17 \times 10^3$ $M^{-1}$) (ca. 120%) compared to that (Ksv=998 $M^{-1}$) for benzoquinone. This result indicates that polysilole 1 exhibits less response to interferences and greater response to nitroaromatic compounds compared to the pentiptycene-derived polymer 13.

Statistical Estimates of Detection Limit From Extrapolation of Stern-Volmer Quenching Data From Stern-Volmer Quenching Data
Of $\log(I_0/I)-1$ vs [TNT] in ppb.
This corresponds to an extrapolated detection limit of ~1.5 ppt for instant detection with our fluorescence spectrometer at the 95% confidence limit. Of course, this is for solution data and with a spectrometer, which is not optimized for detection at a single wavelength.

Example

All synthetic manipulations were carried out under an atmosphere of dry dinitrogen gas using standard vacuum-line Schlenk techniques. All solvents were degassed and purified prior to use according to standard literature methods: diethyl ether, hexanes, tetrahydrofuran, and toluene purchased from Aldrich Chemical Co. Inc. were distilled from sodium/benzophenone ketal. Spectroscopic grade of toluene from Fisher Scientific was used for the fluorescent measurement. NMR grade deuteriochloroform was stored over 4 Å molecular sieves. All other reagents (Aldrich, Gelest) were used as received or distilled prior to use. NMR data were collected with Varian Unity 300, 400, or 500 MHz spectrometers (300.1 MHz for $^1$H NMR, 75.5 MHz for $^{13}$C NMR and 99.2 MHz for $^{29}$Si NMR) and all NMR chemical shifts are reported in parts per million (δ ppm); downfield shifts are reported as positive values from tetramethylsilane (TMS) as standard at 0.00 ppm. The $^1$H and $^{13}$C chemical shifts are reported relative to CHCl$_3$ (δ 77.0 ppm) as an internal standard, and the $^{29}$Si chemical shifts are reported relative to an external TMS standard.

NMR spectra were recorded using samples dissolved in CDCl$_3$, unless otherwise stated, on the following instrumentation. $^{13}$C NMR were recorded as proton decoupled spectra, and $^{29}$Si NMR were recorded using an inverse gate pulse sequence with a relaxation delay of 30 seconds. The molecular weight was measured by gel permeation chromatography using a Waters Associates Model 6000A liquid chromatograph equipped with three American Polymer Standards Corp. Ultrastyragel columns in series with porosity indices of $10^3$, $10^4$, and $10^5$ Å, using freshly distilled THF as eluent.

The polymer was detected with a Waters Model 440 ultraviolet absorbance detector at a wavelength of 254 nm, and the data were manipulated using a Waters Model 745 data module. Molecular weight was determined relative to calibration from polystyrene standards. Fluorescence emission and excitation spectra were recorded on a Perkin-Elmer Luminescence Spectrometer LS 50B. Monomers, 1,1-dichloro-2,3,4, 5-tetraphenylsilole, 1,1-dichloro-2,3,4,5-tetraphenylgermole, 1,1-dilithio-2,3,4,5-tetraphenylsilole, and 1,1-dilithio-2,3,4,5-tetraphenylgermole were synthesized by following the procedures described in the literature. All reactions were performed under Ar atmosphere.

Polymetalloles 1, 2, and 3 were synthesized by following the procedures described in the literature.

Preparation of Silole-Silane Copolymers, (Silole-SiR$^1$R$^2$)$_n$

Stirring of 1,1-dichloro-2,3,4,5-tetraphenylsilole (5.0 g, 11.0 mmol) with lithium (0.9 g, 129.7 mmol) in TEF (120 mL) for 8 h at room temperature gave a dark yellow solution of silole dianion. After removal of excess lithium, 1 mol equiv of corresponding silanes, R$^1$R$^2$SiCl$_2$ (11.0 mmol) was added slowly to a solution of tetraphenylsilole dianion, and stirred at room temperature for 2 hours. The resulting mixture was refluxed for 3 days. The reaction mixture was cooled to room temperature and quenched with methanol. Then the volatiles were removed under reduced pressure. THF (20 mL) was added to the residue and polymer was precipitated by slow addition of the solution into 700 mL of methanol. The third cycle of dissolving-precipitation followed by freeze-drying gave the polymer as yellow powder.

For (silole)$_n$(SiMeH)$_m$(SiPhH)$_o$, each 5.5 mmol of SiMeHCl$_2$ and SiPhHCl$_2$ were slowly added into a THF solution of silole dianion. In case of (silole-SiH$_2$)$_m$, after addition of the xylene solution of SiH$_2$Cl$_2$ (11.0 mmol), the resulting mixture was stirred for 3 days at room temperature instead of refluxing.

Selected data for (silole-SiMeH)$_n$, 4; Yield=2.10 g (44.5%); $^1$H NMR (300.134 MHz, CDCl$_3$): δ=−0.88-0.60 (br. 3H, Me), 3.06-4.89 (br. 1H, SiH, 6.16-7.45 (br. 20H, Ph); $^{13}$C{H} NMR (75.469 MHz, CDCl$_3$): δ=0.61-1.69 (br. Me), 123.87-131.75, 137.84-145.42, 153.07-156.73 (br. m, Ph); $^{29}$Si NMR (71.548 MHz, inversed gated decoupling, CDCl$_3$): δ=−29.22 (br. silole), −66.61 (br. SiMeH). GPC: Mw=4400, Mw/Mn=1.04. Fluorescence (conc.=10 mg/L); $λ_{em}$=492 nm at $λ_{ex}$=340 nm.

Selected data for (silole-SiPhH)$_n$, 5; Yield=2.00 g (37.0%); $^1$H NMR (300.134 MHz, CDCl$_3$): δ=3.00-4.00 (br. 1H, SiH), 6.02-7.97 (br. 20H, Ph); $^{13}$C{H} NMR (75.469 MHz, CDCl$_3$): δ=123.64-143.98, 152.60-157.59 (br. m, Ph); $^{29}$Si NMR (71.548 MHz, inversed gated decoupling, CDCl$_3$): δ=−37.51 (br. silole), −71.61 (br. SiPhH). GPC: Mw=4500, Mw/Mn=1.09, determined by SEC with polystyrene standards; Fluorescence (conc.=10 mg/L); $λ_{em}$=487 nm at $λ_{ex}$=340 nm.

Selected data for (silole)$_n$(SiMeH)$_{0.5n}$(SiPhH)$_{0.5n}$, 6; Yield=2.10 g (41.5%); $^1$H NMR (300.134 MHz, CDCl$_3$): δ=−0.67-0.40 (br. 3H, Me), 3.08-4.98 (br. 2H, SiH, 6.00-7.82 (br. 55H, Ph); $^{13}$C{H} NMR (75.469 MHz, CDCl$_3$): δ=−0.85-1.76 (br. Me), 122.06-147.25, 153.11-157.26 (br. m, Ph); $^{29}$Si NMR (71.548 MHz, inversed gated decoupling, CDCl$_3$): δ=−28.61 (br. silole), −59.88 (br. SiMeH and SiPhH). GPC: Mw=4800, Mw/Mn=1.16, determined by SEC with polystyrene standards; Fluorescence (conc.=10 mg/L); $λ_{em}$=490 nm at $λ_{ex}$=340 nm.

Selected data for (silole-SiH$_2$)$_n$, 8; Yield=2.05 g (44.9%); $^1$H NMR (300.134 MHz, CDCl$_3$): δ=3.00-4.96 (br. 2H, SiH$_2$), 6.12-7.72 (br. 20H, Ph); $^{13}$C{H} NMR (75.469 MHz, CDCl$_3$): δ=122.08-132.78, 136.92-146.25, 152.81-160.07 (br. m, Ph); $^{29}$Si NMR (71.548 MHz, inversed gated decoupling, CDCl$_3$): δ=−30.95 (br. silole), −51.33 (br. SiH$_2$). ratio of n:m=1.00:0.80; GPC: Mw=4600, Mw/Mn=1.14, determined by SEC with polystyrene standards; Fluorescence (conc.=10 mg/L); $λ_{em}$=499 nm at $λ_{ex}$=340 nm.

Selected data for (silole-SiPh$_2$)$_n$, 7; Yield=2.93 g (47.0%); $^1$H NMR (300.134 MHz, CDCl$_3$): δ=6.14-7.82 (br. 20H, Ph); $^{13}$C{H} NMR (75.469 MHz, CDCl$_3$): δ=122.08-146.25 (br. m, Ph), 152.81-160.07 (silole ring); GPC: Mw=5248, Mw/Mn=1.05, determined by SEC with polystyrene standards; Fluorescence (conc.=10 mg/L); $λ_{em}$=492 nm at $λ_{ex}$=340 nm.

Preparation of Germole-Silane Copolymers, (Germole-SiR$^1$R$^2$)$_n$

The procedure for synthesizing all germole-silane copolymers was similar to that for silole-silane copolymers. For (germole)$_n$(SiMeH)$_{0.5n}$(SiPhH)$_{0.5n}$, each 5.0 mmol of SiMeHCl$_2$ and SiPhHCl$_2$ were added slowly into a THF solution of germole dianion. The resulting mixture was stirred for 3 days at room temperature.

Selected data for (germole-SiMeH)$_n$, 9; Yield=2.03 g (43%); $^1$H NMR (300.134 MHz, CDCl$_3$): δ=−0.21-0.45 (br. 2.4H, Me), 5.14-5.40 (br. 0.8H, SiH), 6.53-7.54 (br. 20H, Ph); $^{13}$C{H} NMR (75.469 MHz, CDCl$_3$): δ=−9.70--8.15 (br. Me), 125.29-130.94, 139.08-148.12, 151.29-152.88 (br. m, Ph); $^{29}$Si NMR (71.548 MHz, inversed gated decoupling, CDCl$_3$): δ=−50.40 (br. SiMeH); GPC: Mw=4900, Mw/Mn=1.12, determined by SEC with polystyrene standards; UV (conc.=10 mg/L); $δ_{abs}$=296, 368 nm; Fluorescence (conc.=10 mg/L); $λ_{em}$=401, 481 nm at $λ_{ex}$=340 nm.

Selected data for (germole-SiPhH)$_n$, 10; Yield=2.13 g (40%); $^1$H NMR (300.134 MHz, CDCl$_3$): δ=4.71 (br. 1.0H, SiH), 6.30-7.60 (br. 25H, Ph); $^{13}$C{H} NMR (75.469 MHz, CDCl$_3$): δ=125.50-144.50, 151.50-153.00 (br. m, Ph); $^{29}$Si NMR (71.548 MHz, inversed gated decoupling, CDCl$_3$): δ=−56.81 (br. SiPhH); GPC: Mw=4400, Mw/Mn=1.06, determined by SEC with polystyrene standards; UV (conc.=10 mg/L); $λ_{abs}$=294, 362 nm; Fluorescence (conc.=10 mg/L); $λ_{em}$=401, 486 nm at $λ_{ex}$=340 nm.

Selected data for (germole)$_n$(SiMeH)$_{0.5n}$(SiPhH)$_{0.5n}$11; Yield=2.01 g (40%); $^1$H NMR (300.134 MHz, CDCl$_3$): δ=−0.04-0.42 (br. 3H, Me), 4.94 (br. 2H, SiH), 6.33-7.66 (br. 25H, Ph); $^{13}$C{H} NMR (75.469 MHz, CDCl$_3$): δ=124.31-130.66, 138.43-152.54 (br. m, Ph); $^{29}$Si NMR (71.548 MHz, inversed gated decoupling, CDCl$_3$): δ=−63.01 (br. SiMeH and SiPhH): 0.71; GPC: Mw=4100, Mw/Mn=1.06, determined by SEC with polystyrene standards; UV (conc.=10 mg/L); $\lambda_{abs}$=290, 364 nm; Fluorescence (conc.=10 mg/L); $\lambda_{em}$=399, 483 nm at $\lambda_{ex}$=340 nm.

Selected data for (germole-SiPh$_2$)$_n$, 12; Yield=3.23 g (48%); $^1$H NMR (300.134 MHz, CDCl$_3$): δ=6.21-7.68 (br. 30H, Ph); $^{13}$C{H} NMR (75.469 MHz, CDCl$_3$): δ=125.15-141.40 (br. m, Ph), 151.12-153.99 (germole ring carbon); GPC: Mw=5377, Mw/Mn=1.09, determined by SEC with polystyrene standards; UV (conc.=10 mg/L); $\lambda_{abs}$=298, 366 nm; Fluorescence (conc.=10 mg/L); $\lambda_{em}$=400, 480 nm at $\lambda_{ex}$=340 nm.

Preparations for other metallole-silane and metallole-germane copolymers such as tetraalkylmetallole-silane copolymers and tetraarylmetallole-germane copolymers can be prepared by the above method described.

Preparation of Poly(tetraphenyl)silole and Poly(tetraphenyl)germole By Catalytic Dehydrocoupling Preparation of polymetallole: 1,1-dihydro-2,3,4,5-tetraphenylsilole or germole were prepared from the reduction of 1,1-dichloro-2,3,4,5-tetraphenylsilole or germole with 1 mol equiv of LiAlH$_4$. Additionally, an alternate method to prepare the dihydrometallole is to add dichlorosilane (25% in xylenes) to an solution of tetraphenylbutadiene dianion in ether, as described in the literature. Reaction conditions for preparing the polygermole are the same as those for polysilole. 1,1-dihydro-2,3,4,5-tetraphenylsilole (1.0 g, 2.59 mmol) and 1-5 mol % of RhCl(PPh$_3$)$_3$ or Pd(PPh$_3$)$_4$ in toluene (10 mL) were placed under an Ar atmosphere and degassed through 3 freeze-pump-thaw cycles. The reaction mixture was vigorously refluxed for 72 h. The solution was passed rapidly through a Florisil column and evaporated to dryness under Ar atmosphere. 1 mL of THF was added to the reaction mixture and the resulting solution was then poured into 10 mL of methanol. Poly(tetraphenyl)silole, 1, was obtained as a pale yellow powder after the third cycle of dissolving-precipitation followed by freeze-drying. An alternative method for poly(tetraphenyl)silole preparation is as follows. 1,1-dihydro-2,3,4,5-tetraphenylsilole (1.0 g, 2.59 mmol) and 0.1-0.5 mol % H$_2$PtCl$_6$.xH$_2$O and 2-5 mol equivalents of allylamine in toluene (10 mL) were vigorously refluxed for 24 hours. The solution was passed through a sintered glass frit and evaporated to dryness under an Ar atmosphere. Three dissolving-precipitation cycles with THF and methanol were performed as stated above to obtain 1. The molecular weights of polymers were obtained by GPC. 1,1-dihydro-2,3,4,5-tetraphenylsilole with RhCl(PPh$_3$)$_3$, 1: isolated yield=0.81 g, 82%, M$_w$=4355, M$_w$/Mn=1.02, determined by SEC with polystyrene standards; 1,1-dihydro-2,3,4,5-tetraphenylsilole with Pd(PPh$_3$)$_4$, 1: 0.84 g, 85%, M$_w$=5638, M$_w$/M$_n$=1.10). 1,1-dihydro-2,3,4,5-tetraphenylgermole with RhCl(PPh$_3$)$_3$, poly(tetraphenyl)germole: 0.80 g, 81%, M$_w$=3936, M$_w$/M$_n$=1.01; 1,1-dihydro-2,3,4,5-tetraphenylgermole with Pd(PPh$_3$)$_4$, poly(tetraphenyl)germole: 0.81 g, 82%, M$_w$=4221, M$_w$/M$_n$=1.02) $^1$H NMR (300.133 MHz, CDCl$_3$): δ=6.30-7.90 (br, m, Ph); $^{13}$C(H) NMR (75.403 MHz, CDCl$_3$ (δ=77.00)): δ=124-130 (br, m, Ph), 131-139 (germole carbons). If less vigorous reflux conditions are used, with the RhCl(PPh$_3$)$_3$ and Pd(PPh$_3$)$_4$ catalysts, then corresponding dimers form along with lesser amounts of polymer. The dimer is less soluble and crystallizes from toluene.

Preparation of Poly(1,4-diethynylbenzene)2,3,4,5-tetraphenylsilole (PDEBsilole)

1,1 dihydro-2,3,4,5-tetraphenylsilole (250 mg, 0.65 mmol), 1,4-diethynylbenzene (100 mg, 0.80 mmol), and 0.1-0.5 mol % H$_2$PtCl$_6$.xH$_2$O were vigorously refluxed in toluene (10 mL), under argon for 4 hours. The dark orange solution was passed through a sintered glass frit and evaporated to dryness. The remaining solid was dissolved in 1 ml of THF, precipitated with 10 ml of methanol, and collected by filtration on a sintered glass frit. The precipitation was repeated twice more and the polymer was obtained as a yellow solid (0.17 g, 51%). The molecular weight of the polymer was determined by GPC with polystyrene standards. M$_w$=6,198, M$_w$/M$_n$=1.822; $^1$H NMR (300.075 MHz, CDCl$_3$): δ 6.60-7.20 (br, 24H, silole Ph, =CH–Si, And =CH–Ph), δ 7.40 (br, 4H, phenylene Ph); UV (conc.=20 mg/L); $\lambda_{abs}$=302, 378 nm; Fluorescence (conc. 20 mg/L); $\lambda_{em}$=500 nm ($\lambda_{ex}$=360 nm).

Preparation of Poly(1,4-diethynylbenzene)2,3,4,5-tetraphenylgermole (PDEBgermole)

1,1-dihydro-2,3,4,5-tetraphenylgermole (100 mg, 0.23 mmol), 1,4-diethynylbenzene (34 mg, 0.26 mmol), and 0.1-0.5 mol % H$_2$PtCl$_6$.xH$_2$O were vigorously refluxed in toluene (10 mL), under argon for 12 hours. The catalyst was removed by filtration, and the filtrate then evaporated to dryness. The remaining solid was dissolved in THF (1 mL) and precipitated by subsequent addition of methanol (10 mL). The polymer was collected by filtration and dried to afford the yellow powder (0.095 g, 73%). Molecular weights determined by GPC: M$_w$=4800, M$_w$/M$_n$=1.6; $^1$H NMR (300.075 MHz, CDCl$_3$): δ 6.50-7.60 (br, silole Ph, =CH—Ge, and =CH-Ph, phenylene H); UV-Vis (Toluene): $\lambda_{abs}$=290, 362 nm; Fluorescence (Toluene): $\lambda_{em}$=475 nm ($\lambda_{ex}$=360 nm).

Preparation of Poly(1,4-diethynylbenzene)silafluorene (PDEBSF)

1,1 dihydrosilafluorene (0.25 g, 1.37 mmol), 1,4-diethynylbenzene (0.19 g, 1.51 mmol), and 0.1-0.5 mol % H$_2$PtCl$_6$.xH$_2$O were vigorously refluxed in toluene (3 mL), under argon for 24 hours. The dark orange/red solution was filtered and evaporated to dryness. The remaining solid was dissolved in 4 ml of THF, precipitated with 40 ml of methanol. The white solid (0.17 g, 34%) was collected by filtration on a sintered glass frit. The molecular weight of the polymer was determined by GPC with polystyrene standards. M$_w$=1,957, M$_w$/M$_n$=1.361; $^1$H NMR (300.075 MHz, CDCl$_3$): δ 6.00-8.00 (br, 16H, silafluorene H-Ph, =CH—Si, and =CH-Ph); UV (conc.=20 mg/L); $\lambda_{abs}$=292 nm; Fluorescence (conc. 0.2 mg/L); $\lambda_{em}$=341, 353 nm at $\lambda_{ex}$=292 nm.

Preparation And Characterization of Polysilafluorene (PSF)

The high energy of the excited state in the UV luminescent polysilafluorene offers an increased driving force for electron transfer to the explosive analyte and improved detection limits by electrontransfer quenching, which should be applicable for any UV emitting conjugated organic or inorganic polymer.

1,1-dihydrosilafluorene (500 mg, 2.7 mmol) and 0.5 mol % $H_2PtCl_6 \cdot xH_2O$ were stirred in toluene (3 mL) at 80° C. under argon for 24 hours. The orange-brown solution was filtered while warm and evaporated to dryness. The remaining solid was dissolved in 3 mL of THF and precipitated with the addition of 30 mL of methanol. The resulting light orange-white solid was collected by vacuum filtration (0.101 g, 20%). The molecular weight of the polymer was determined by GPC with polystyrene standards. $M_w=576$, $M_w/M_n=1.074$; $^1H$ NMR (300.075 MHz, $CDCl_3$): δ 6.60-7.90 (br, 8H, silafluorene H-Ph), δ 4.62 (weak s, terminal Si—H); UV (conc.=20 mg/L); $\lambda_{abs}=392$ nm; Fluorescence (conc. 0.2 mg/L); $\lambda_{em}=342$, 354 nm, at $\lambda_{ex}=292$ nm.

Detection limits of trinitrotoluene (TNT), dinitrotoluene (DNT), picric acid (PA), 2,2'-dimethyl-2,2'-dinitrobutane (DMNB), orthomononitrotoluene (OMNT), and paramononitrotoluene (PMNT) were determined by fluorescence quenching of polysilole, polyDEBsilole, polygermole, polyDEBgermole, PSF, polyDEBSF, and ExPray. (DEB=diethynylbenzene.) The emission of PSF is centered in the UV, so detection limits with a UV camera are expected to be even better than those determined visually.

Preparation And Characterization of Polygermafluorene (PGF)

1,1-dihydrogermafluorene (0.1 g, 0.44 mmol) and 0.5 mol % $H_2PtCl_6 \cdot xH_2O$ were refluxed in toluene (4 mL) under argon for 24 hours. The thick orange solution was filtered while warm and evaporated to dryness. The remaining solid was dissolved in 2 mL of THF and precipitated with 22 mL of methanol. The resulting light orange-white solid was collected by vacuum filtration (0.010 g, 10%). The molecular weight of the polymer was determined by GPC with polystyrene standards. $M_w=890$, $M_w/M_n=1.068$; $^1H$ NMR (300.075 MHz, $CDCl_3$): δ 6.40-7.90 (br, 8H, silafluorene H-Ph).

Preparation And Characterization of Poly(1,4-diethynylbenzene)germafluorene (PDEBGF)

1,1 dihydrogermafluorene (0.15 g, 0.66 mmol), 1,4-diethynylbenzene (0.092 g, 0.73 mmol), and 0.1-0.5 mol % $H_2PtCl_6 \cdot xH_2O$ were vigorously refluxed in toluene (4 mL), under argon for 24 hours. The dark orange-red solution was filtered and evaporated to dryness. The remaining solid was dissolved in 4 ml of THF and precipitated with 40 ml of methanol. The light orange solid (0.021 g, 15%) was collected by filtration on a sintered glass frit. The molecular weight of the polymer was determined by GPC with polystyrene standards. $M_w=1,719$, $M_w/M_n=1.872$; $^1H$ NMR (300.075 MHz, $CDCl_3$): δ 6.00-8.00 (br, 16H, germafluorene H-Ph, =CH—Si, and =CH-Ph).

Experimental Results And Data

The method of explosives detection is through luminescence quenching of the metallole-containing polymers by the nitroaromatic analyte. Three common explosives were tested, Trinitrotoluene (TNT), 2,4-dinitrotoluene (DNT), and picric acid (PA). Stock solutions of the explosives were prepared in toluene. Aliquots (1-5 μL) of the stock (containing 5 to 100 ng analyte) were syringed onto either Whatman filter paper or a CoorsTek® porcelain spot plate and allowed to dry completely. The spots were between 3 and 10 mm in diameter, producing a surface concentration of not more than 64 ng/cm$^2$ and not less than 17 ng/cm$^2$. Solutions of the polymers (0.5-1% w:v) were prepared in acetone (PSi, PGe), 1:1 toluene:acetone (PDEBGe), 2:1 toluene:acetone (PDEBSi), or toluene (PDEBSF). A thin film of a polymer was applied to the substrate by spray coating a polymeric solution onto the substrate and air drying. The coated substrates were placed under a black light to excite the polymer fluorescence. Dark spots in the film indicate luminescence quenching of the polymer by the analyte. The process was carried out for each of the three explosive analytes with each of the six polymers on both substrates.

Results And Discussion

Nitroaromatic explosives may be visually detected in nanogram quantities by fluorescence quenching of photoluminescent metallole-containing polymers. Detection limits depend on the nitroaromatic analyte as well as on the polymer used.

FIG. 22 summarizes the detection limits of TNT, DNT, and picric acid using the five metallole-containing polymers synthesized, PSi, PDEBSi, PGe, PDEBGe, PSF and PDEBSF.

In all cases, the detection limit of the explosives was as low or lower on the porcelain than on paper, likely because the solvated analyte may be carried deep into the fibers of the paper during deposition, thus lowering the surface contamination after solvent evaporation. Less explosive would be present to visibly quench the thin film of polymer on the surface. This situation is less pronounced in actuality when explosives are not deposited via drop-casting from an organic solution, but handled as the solid. Illumination with a black light ($\lambda_{ex}$~360 nm) excites the polymer fluorescence near 490-510 nm for the siloles, 470-500 for germoles. The silafluorene luminescence, which peaks at 360 nm, is very weak in the visible region, but it is sufficient for visible quenching.

Figure 23:
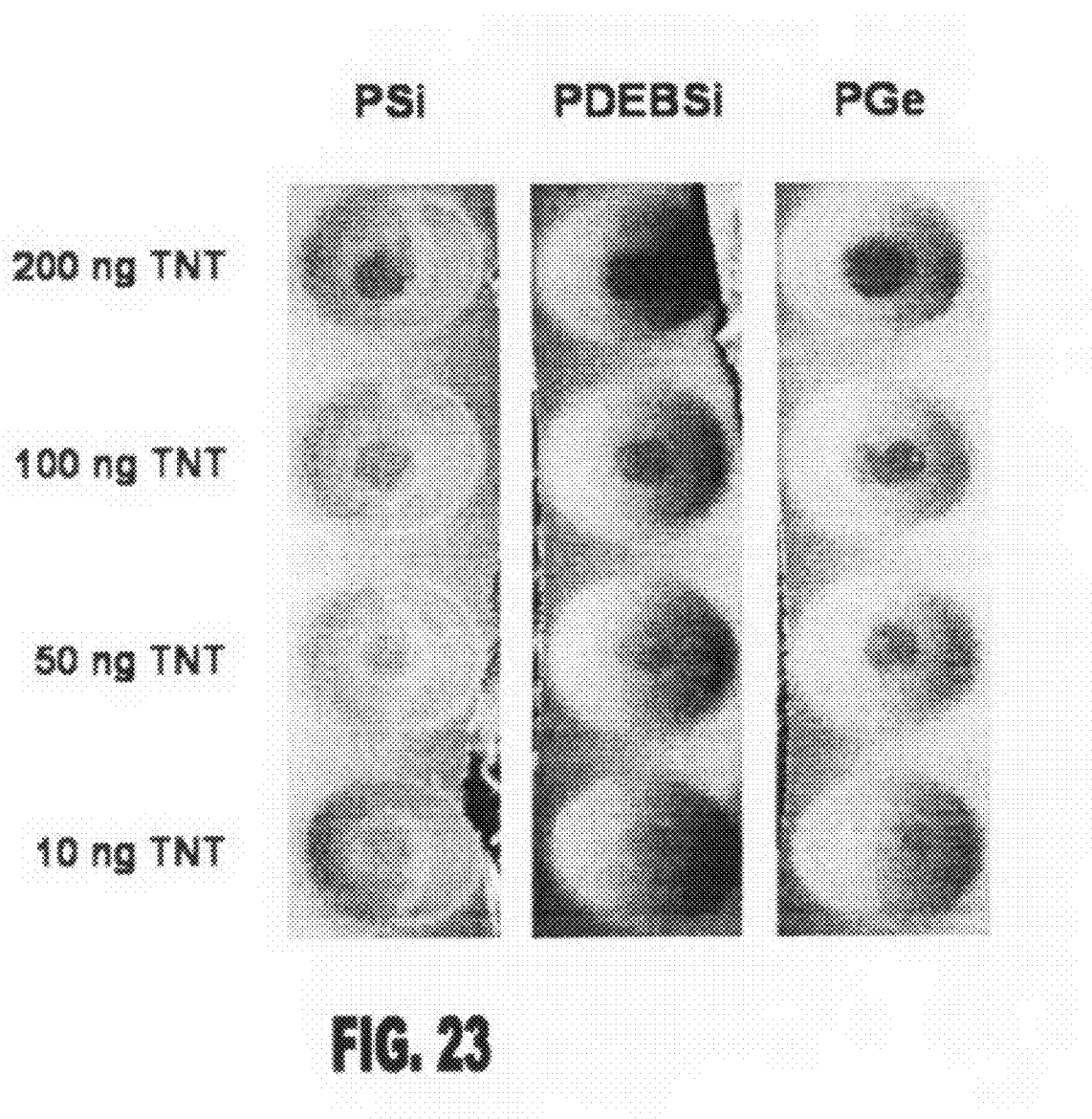
FIG. 23 are black and white images of the luminescence quenching of three polymers, PSi, PDEBSi, and PGe, by 200, 100, 50, and 10 ng TNT on porcelain plates as observed on a porcelain plate.
Figure 24:
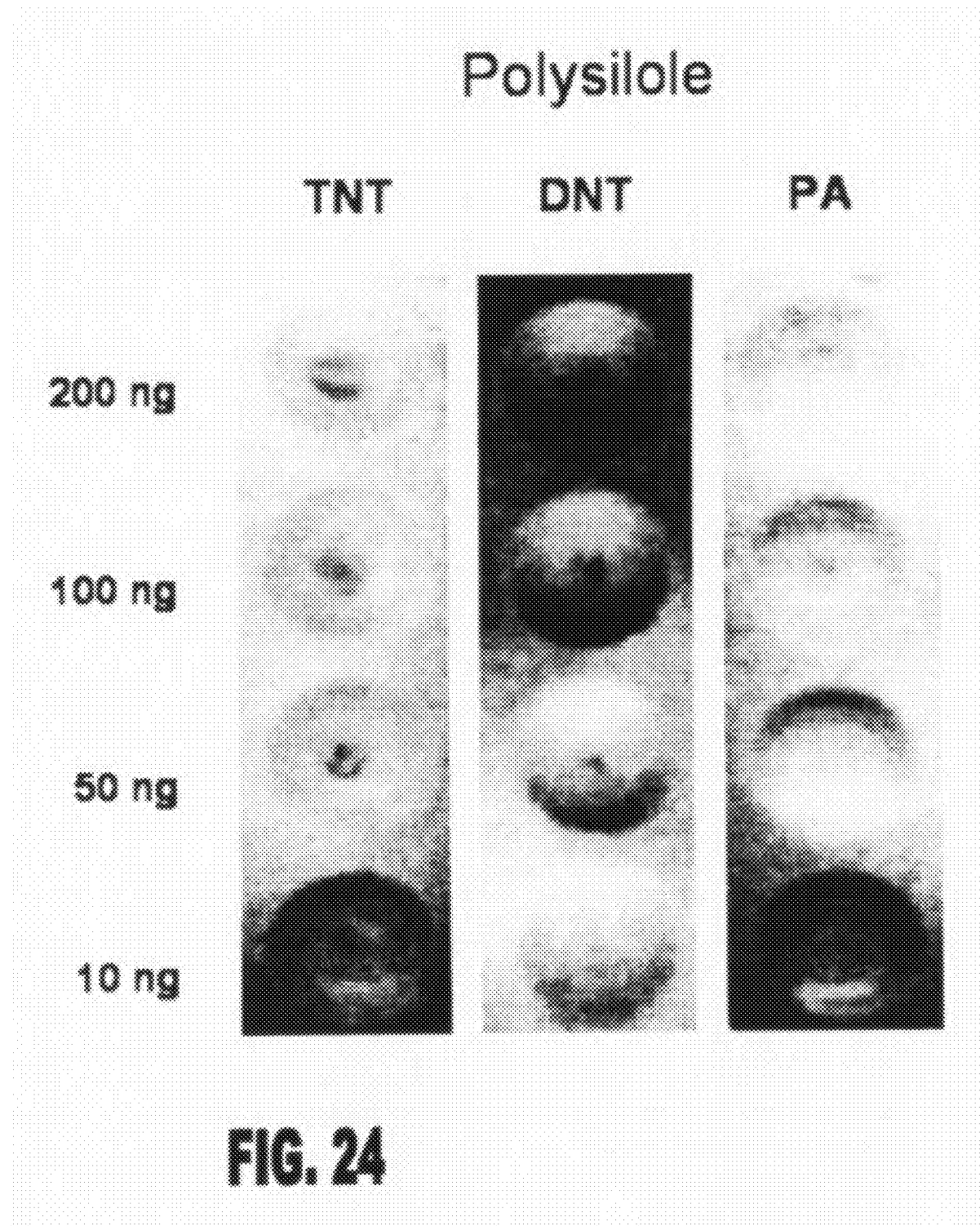
FIG. 24 are exemplary black and white images of the luminescence quenching of polysilole by each analyte at different surface concentrations.

FIG. 23 shows a sample black and white images of the luminescence quenching of three polymers, PSi, PDEBSi, and PGe, by 200, 100, 50, and 10 ng TNT on porcelain plates as observed on a porcelain plate. FIG. 24 shows sample black and white images of the luminescence quenching of polysilole by each analyte at different surface concentrations.

The method of detection is through electron-transfer luminescence quenching of the polymer luminescence by the nitroaromatic analytes. Consequently, the ability of the polymers to detect the explosives depends on the oxidizing power of the analytes. The oxidation potentials of the analytes follow the order TNT>PA>DNT. Both TNT and PA have three nitro substituents on the aromatic ring which account for their higher oxidizing potential relative to DNT, which has only two nitroaromatic substituents. PA has a lower oxidation potential than TNT due to the electron donating power of the hydroxy substituent. The molecular structure accounts for the lowest detection limit for TNT, followed by PA and DNT.

Luminescence quenching is observed immediately upon illumination. The polymers are photodegradable, however, and luminescence begins to fade after a few minutes of continual UV exposure. Nevertheless, these polymers present an inexpensive and simple means to detect low nanogram level of nitroaromatic explosives.

While various embodiments of the present invention have been shown and described, it should be understood that modifications, substitutions, and alternatives are apparent to one of ordinary skill in the art. Such modifications, substitutions, and alternatives can be made without departing from the spirit and scope of the invention, which should be determined from the appended claims.

Various features of the invention are set forth in the appended claims.

What is claimed is:

1. A method for detecting an analyte that may be present in ambient air, on a surface or as part of complex aqueous media comprising:
providing an inorganic-organic metallole-containing polymer or copolymer with a backbone including carbon atoms bonded to metalloid atoms;
exposing said polymer or copolymer to a suspected analyte or a system suspected of including the analyte; and
measuring a quenching of photoluminescence of said polymer or copolymer exposed to said system.

2. The method of claim 1 further comprising selecting the polymer or copolymer to be one of the group consisting of PDEBSi, PDEBGe, PDEBSF, and PDEBGF.

3. The method of claim 1 wherein the polymer or copolymer is cast as a thin film.

4. The method of claim 3 wherein the thin film is deposited on a solid surface.

5. The method of claim 1 wherein the polymer or copolymer is sprayed onto a solid surface having the analyte disposed thereon to form a thin film of the polymer or copolymer on the solid surface.

6. The method of claim 5 wherein the solid surface comprises one of glass, paper, metal, plastic, porcelain or wood.

7. The method of claim 1 wherein said step of exposing said polymer or copolymer comprises submerging the polymer or copolymer in an aqueous solvent.

8. The method of claim 1 wherein said step of exposing the polymer or copolymer comprises submerging the polymer or copolymer in an organic solvent.

9. The method of claim 1 wherein said step of measuring a quenching of photoluminescence includes illuminating the polymer or copolymer with light having a wavelength of between 250 nm and 420 nm and observing photoluminescence quenching.

10. The method of claim 1 wherein said step of measuring a quenching of photoluminescence includes subjecting said polymer or copolymer to fluorescence spectrometry.

11. The method of claim 1 wherein the metallole-containing polymer or copolymer is provided as an inorganic-organic polymer sensor that comprises a substrate and a thin film of the metallole-containing polymer or copolymer deposited on the substrate.

12. A method for detecting an analyte that may be present in ambient air, on a surface or as part of complex aqueous media comprising:
providing an inorganic-organic metallole-containing polymer or copolymer, said polymer or copolymer being a synthesis product of hydrosilation or hydrogermylation of an organic dialkene or dialkyne by a dihydrometallole;
exposing said polymer or copolymer to a suspected analyte or a system suspected of including the analyte; and
measuring a quenching of photoluminescence of said polymer or copolymer exposed to said system.

* * * * *

UNITED STATES PATENT AND TRADEMARK OFFICE
CERTIFICATE OF CORRECTION

PATENT NO. : 7,927,881 B2
APPLICATION NO. : 11/990832
DATED : April 19, 2011
INVENTOR(S) : Trogler et al.

It is certified that error appears in the above-identified patent and that said Letters Patent is hereby corrected as shown below:

In the Abstract:
Line 1    Please delete "analyze" and insert --analyte-- therefor.
Line 5    Please delete "analyze" and insert --analyte-- therefor.
Line 6    Please delete "analyze" and insert --analyte-- therefor.

In the Specification:
Col. 2, line 38    After "germole" please delete "2." and insert --2,-- therefor.
Col. 2, line 56    Please delete "♦ (DNT)" and insert --▲ (DNT)-- therefor.
Col. 2, line 63    Please delete "♦ (polymer 4)" and insert --▲ (polymer 4)-- therefor.
Col. 3, line 12    Please delete "♦ (polymer 3)" and insert --▲ (polymer 3)-- therefor.
Col. 3, line 13    Please delete "✪ (polymer 5)" and insert -- *(polymer 5)-- therefor.
Col. 3, line 13    Please delete "and (polymer 10)" and insert --and – (polymer 10)-- therefor.
Col. 4, line 66    Please delete "exhibit (σ* - σ*"" and insert --exhibit σ* - σ*-- therefor.
Col. 5, line 27    Please delete "Poly(1,4diethynylbenzene)" and insert --Poly(1,4-diethynylbenzene)-- therefor.
Col. 5, line 66    Please delete "$H_2PtCl_6.xH_2O$" and insert --$H_2PtCl_6 \cdot xH_2O$-- therefor.
Col. 6, line 42    Please delete "an" and insert --a-- therefor.
Col. 7, line 9     Please delete "Ph2C4SiH2" and insert --$Ph_2C_4SiH_2$-- therefor.
Col. 7, line 14    Please delete "σ - (σ2*" and insert --σ - ($σ_2$*-- therefor.
Col. 7, line 34    Please delete "89.760" and insert --89.76°-- therefor.
Col. 10, line 39   Please delete "(Ksv=674 $M^{-1})^{-1}$" and insert --($K_{sv}$=674 $M^{-1}$)-- therefor.
Col. 11, line 43   Please delete "TEF" and insert --THF-- therefor.
Col. 12, line 15   Please delete "(br. 2H, SiH," and insert --(br. 2H, Si$\underline{H}$),-- therefor.
Col. 13, line 1    Please delete "(germole)$_n$(SiMeH)$_{0.5n}$(SiPhH)$_{0.5n}$11;" and insert --(germole)$_n$(SiMeH)$_{0.5n}$(SiPhH)$_{0.5n}$,11;-- therefor.
Col. 13, line 33   Please delete "an solution" and insert --a solution-- therefor.
Col. 13, line 49   Please delete "$H_2PtCl_6.xH_2O$" and insert --$H_2PtCl_6 \cdot xH_2O$-- therefor.
Col. 13, line 65   Please delete "$^{13}C(H)$" and insert --$^{13}C\{H\}$-- therefor.

Signed and Sealed this
Eleventh Day of October, 2011

David J. Kappos
*Director of the United States Patent and Trademark Office*

| | |
|---|---|
| Col. 14, line 1 | Please delete "RhCI(PPh$_3$)$_3$" and insert --RhCl(PPh$_3$)$_3$-- therefor. |
| Col. 14, line 10 | Please delete "H$_2$PtCl$_6$.xH$_2$O" and insert --H$_2$PtCl$_6$·xH$_2$O-- therefor. |
| Col. 14, line 21 | After "CH-Si," please delete "And" and insert --and-- therefor. |
| Col. 14, line 30 | Please delete "H$_2$PtCl$_6$.xH$_2$O" and insert --H$_2$PtCl$_6$·xH$_2$O-- therefor. |
| Col. 14, line 47 | Please delete "H$_2$PtCl$_6$.xH$_2$O" and insert --H$_2$PtCl$_6$·xH$_2$O-- therefor. |
| Col. 14, line 65 | Please delete "electrontransfer" and insert --electron transfer-- therefor. |
| Col. 15, line 2 | Please delete "H$_2$PtCl$_6$.xH$_2$O" and insert --H$_2$PtCl$_6$·xH$_2$O-- therefor. |
| Col. 15, line 28 | Please delete "H$_2$PtCl$_6$.xH$_2$O" and insert --H$_2$PtCl$_6$·xH$_2$O-- therefor. |
| Col. 15, line 44 | Please delete "H$_2$PtCl$_6$.xH$_2$O" and insert --H$_2$PtCl$_6$·xH$_2$O-- therefor. |
| Col. 16, line 37 | After "shows" please delete "a". |